US010745687B2

(12) United States Patent
Ramiya

(10) Patent No.: US 10,745,687 B2
(45) Date of Patent: Aug. 18, 2020

(54) METHODS OF POLYNUCLEOTIDE PREPARATION USING MULTIVALENT CATION SALT COMPOSITIONS

(71) Applicant: Geron Corporation, Menlo Park, CA (US)

(72) Inventor: Premchandran H. Ramiya, San Ramon, CA (US)

(73) Assignee: Geron Corporation, Foster City, CA (US)

( * ) Notice: Subject to any disclaimer, the term of this patent is extended or adjusted under 35 U.S.C. 154(b) by 489 days.

(21) Appl. No.: 15/134,740

(22) Filed: Apr. 21, 2016

(65) Prior Publication Data

US 2016/0312227 A1   Oct. 27, 2016

Related U.S. Application Data

(60) Provisional application No. 62/151,891, filed on Apr. 23, 2015.

(51) Int. Cl.
*C12N 15/10* (2006.01)
*C12N 15/113* (2010.01)

(52) U.S. Cl.
CPC ....... *C12N 15/1003* (2013.01); *C12N 15/101* (2013.01); *C12N 15/113* (2013.01); *C12N 15/1137* (2013.01); *C12N 2310/113* (2013.01); *C12N 2310/3145* (2013.01); *C12N 2310/3515* (2013.01)

(58) Field of Classification Search
CPC .......................... C12N 15/1003; C12N 15/101
USPC ......................................................... 536/25.4
See application file for complete search history.

(56) References Cited

U.S. PATENT DOCUMENTS

| 4,046,720 | A | 9/1977 | Rembaum et al. |
| 4,413,070 | A | 11/1983 | Rembaum |
| 4,659,774 | A | 4/1987 | Webb |
| 4,678,814 | A | 7/1987 | Rembaum |
| 5,185,444 | A | 2/1993 | Summerton |
| 5,281,701 | A | 1/1994 | Vinayak |
| 5,476,925 | A | 12/1995 | Letsinger |
| 5,591,607 | A | 1/1997 | Gryaznov et al. |
| 5,599,922 | A | 2/1997 | Gryaznov et al. |
| 5,631,135 | A | 5/1997 | Gryaznov et al. |
| 5,646,260 | A | 7/1997 | Letsinger |
| 5,648,480 | A | 7/1997 | Letsinger |
| 5,684,143 | A | 11/1997 | Gryaznov |
| 5,726,297 | A | 3/1998 | Gryaznov et al. |
| 5,824,793 | A | 10/1998 | Hirschbein et al. |
| 5,837,835 | A | 11/1998 | Gryaznov et al. |
| 5,859,233 | A | 1/1999 | Hirschbein et al. |
| 5,932,718 | A | 8/1999 | Letsinger |
| 5,965,720 | A | 10/1999 | Gryaznov et al. |
| 5,998,604 | A | 12/1999 | Fearon |
| 6,169,170 | B1 | 1/2001 | Gryaznov et al. |
| 6,608,036 | B1 | 8/2003 | Gryaznov et al. |
| 6,835,826 | B2 | 12/2004 | Gryaznov et al. |
| 7,138,383 | B2 | 11/2006 | Gryaznov et al. |
| 7,199,236 | B2 | 4/2007 | Vravikumar et al. |
| 7,485,717 | B2 | 2/2009 | Gryaznov et al. |
| 7,494,982 | B2 | 2/2009 | Gryaznov et al. |
| 7,563,618 | B2 | 7/2009 | Gryaznov et al. |
| 8,748,593 | B2 | 6/2014 | Gryaznov et al. |
| 2007/0117773 | A1 | 5/2007 | Koizumi et al. |
| 2012/0329858 | A1 | 12/2012 | Gryaznov et al. |

FOREIGN PATENT DOCUMENTS

| JP | 2002060341 | 2/2002 |
| WO | 199204384 | 3/1992 |
| WO | 2001018015 | 8/1997 |
| WO | 1998028442 | 7/1998 |
| WO | 1997031009 | 3/2001 |
| WO | 2002077184 | 10/2002 |
| WO | 2004029277 | 4/2004 |
| WO | 2005023994 | 3/2005 |

(Continued)

OTHER PUBLICATIONS

Asai, A. et al., (2003) "A novel telomerase template antagonist (GRN163) as a potential anticancer agent", Cancer Research, 63(14):3931-3939.
Baraniak, J. et al., (1998) "New Approach to the Solid Phase Synthesis of N3'->P5' Phosphoramidate Oligonucleotides", Nucleosides and Nucleotides, 17(8):1347-1353.
Carpino, L. A., (1980) "Convenient preparation of (9-fluorenyl)methanol and its 2,7-dihalo derivatives", The Journal of Organic Chemistry, 45(21):4250-4252.
Carpino, L. A., (1989) "Thioxanthene dioxide based amino-protecting groups sensitive to pyridine bases and dipolar aprotic solvents", The Journal of Organic Chemistry, 54(25):5887-5897.

(Continued)

*Primary Examiner* — Jezia Riley
(74) *Attorney, Agent, or Firm* — Bozicevic, Field & Francis LLP; Rudy J. Ng

(57) ABSTRACT

Aspects of the disclosure include methods for the preparation of a polynucleotide. In some embodiments, the method includes contacting a first polynucleotide composition including: a polynucleotide having a sequence of 7 or more nucleoside subunits and at least two of the nucleoside subunits are joined by a N3'→P5' thiophosphoramidate inter-subunit linkage; and non-target synthetic products and reagents; with a multivalent cation salt to precipitate a polynucleotide salt including at least one multivalent cation counterion; and separating the polynucleotide salt from the contacted first polynucleotide composition to produce a second polynucleotide composition including the polynucleotide salt. In certain embodiments, the method further includes contacting the polynucleotide salt with a reverse phase chromatography support; and eluting from the chromatography support a third polynucleotide composition including the polynucleotide. Also provided are compositions including a salt of the polynucleotide including at least one multivalent cation counterion.

24 Claims, 4 Drawing Sheets

Specification includes a Sequence Listing.

(56) References Cited

FOREIGN PATENT DOCUMENTS

| WO | 2008127305 | 10/2008 |
|---|---|---|
| WO | WO 2012/021985 | 2/2012 |
| WO | WO 2013/170385 | 11/2013 |
| WO | 2014088785 | 6/2014 |
| WO | 2015168310 | 11/2015 |
| WO | 2016/172346 | 10/2016 |

OTHER PUBLICATIONS

Chen, J. et al., (1995) "Synthesis of oligodeoxyribonucleotide N3'->P5' phosphoramidates", Nucleic Acids Research, 23(14):2661-2668.

Escude, C. et al., (1996) "Stable triple helices formed by oligonucleotide N3'->P5' phosphoramidates inhibit transcription elongation", Proceedings of the National Academy of Sciences U.S.A., 93(9):4365-4369.

Froehler, B. C. et al., (1983) "Dialkylformamidines: depurination resistant N6-protecting group for deoxyadenosine", Nucleic Acids Research, 11(22): 8031-8036.

Giovannangeli, C. et al., (1997) "Accessibility of nuclear DNA to triplex-forming oligonucleotides: The integrated HIV-1 provirus as a target", Proceedings of the National Academy of Sciences U.S.A., 94(1):79-84.

Greene, T. W. and Wuts, P. G. M, (1999) "Protection for the hydroxyl group including 1,2- and 1,3- diols" in "Protective Groups in Organic Synthesis", Third Edition, John Wiley and Sons, New York, 17-23, 494-502.

Greene, T. W. and Wuts, P. G. M., (1999) "Protective Groups in Organic Synthesis", John Wiley and Sons, New York, 4-5, 119, 142-143, 513, 550, 559, 583-584.

Greene, T. W. and Wuts, P. G. M., (1999) "Protective Groups in Organic Synthesis", Third Edition, John Wiley and Sons, New York, 588.

Gryaznov, S. and Chen, J., (1994) "Oligodeoxyribonucleotide N3'->P5' Phosphoramidates: synthesis and Hybridization Properties", Journal of the American Chemical Society, 116(7):3143-3144.

Gryaznov, S. et al., (2003) "Oligonucleotide N3'->P5' thiophosphoramidate telomerase template antagonists as potential anticancer agents", Nucleosides Nucleotides Nucleic Acids, 22(5-8):577-581.

Gryaznov, S. M. et al., (1996) "Oligonucleotide N3'->P5' phosphoramidates as antisense agents", Nucleic Acids Research, 24(8):1508-1514.

Gryaznov, S. M. et al., (1995) "Oligonucleotide N3'->P5' phosphoramidates", Proceedings of the National Academy of Sciences USA, 92(13):5798-5802.

Gryaznov, S. M. et al., (1998) "RNA mimetics: oligoribonucleotide N3'->P5' phosphoramidates", Nucleic Acids Research, 26(18): 4160-4167.

Liekens, S. et al., (2004) "The nucleoside derivative 5'-O-trityl-inosine (KIN59) suppresses thymidine phosphorylase-triggered angiogenesis via a noncompetitive mechanism of action", The Journal of Biological Chemistry, 279(28): 29598-29605.

Matray, T. J. et al., (1999) "Synthesis and properties of RNA analogs-oligoribonucleotide N3'->P5' phosphoramidates", Nucleic Acids Research, 27(20):3976-3985.

Mignet, N. and Gryaznov, S. M. et al., (1998) "Zwitterionic oligodeoxyribonucleotide N3'->P5' phosphoramidates: synthesis and properties", Nucleic Acids Research, 26(2): 431-438.

Nakajima, K. et al., (1978) "Studies on Aziridine-2-carboxylic Acid. I. Synthesis of the Optically Active L-Aziridine-2-carboxylic Acid and Its Derivatives", Bull. Chem. Soc. Jpn., 51:1577-1578.

Pongracz, K. and Gryaznov, S. M., (1999) "Oligonucleotide N3'→P5' thiophosphoramidates: synthesis and properties", Tetrahedron Letters, 40(43):7661-7664.

Pongracz, K. et al., (1998) "alpha-Oligodeoxyribonucleotide N3'->P5' phosphoramidates: synthesis and duplex formation", Nucleic Acids Research, 26(4): 1099-1106.

Skorski, T. et al., (1997) "Antileukemia effect of c-myc N3'->P5' phosphoramidate antisense oligonucleotides in vivo", Proceedings of the National Academy of Sciences USA, 94(8):3966-3971.

Ti, G. S. et al., (1982) "Transient Protection: Efficient One-flask Syntheses of Protected Deoxynucleosides", Journal of the American Chemical Society, 104(5):1316-1319.

Vincent, S. et al., (1999) "Hydrolysis and Hydrogenolysis of Formamidines: N,N-Dimethyl and N,N-Dibenzyl Formamidines as Protective Groups for Primary Amines", The Journal of Organic Chemistry, 64(3):991-997.

Vu, H. et al., (1990) "Fast oligonucleotide deprotection phosphoramidite chemistry for DNA synthesis", Tetrahedron Letters, 31(50):7269-7272.

Wang et al., (2004) "Telomerase inhibition with an oligonucleotide telomerase template antagonist: in vitro and in vivo strudies in multiple myeloma and lymphoma", Blood 103(1): 258-266.

Zaitseva, G. V. et al., (1994) "Chemical-Enzymatic Synthesis of 3'-Amino-2', 3'-dideoxy-β-D-ribofuranosides of Natural Heterocyclic Bases and Their 5'-Monophosphates", Nucleosides and Nucleotides, 13(1-3):819-834.

Zhang, B. et al., (2002) "Synthesis of pCpCpA-3'-NH-Phenylalanine as a Ribosomal Substrate", Organic Letters, 4(21):3615-3618.

Zhang, L. et al., (2003) "An Efficient Synthesis of 3'-Amino-3'-deoxyguanosine from Guanosine", Helvetica Chimica Acta, 86(3): 703-710.

Beattie, K. et al., (1993) "Genosensor Technology", Clinical Chemistry, 39(4):719-722.

Chen, J. L. et al., (2000) "Secondary structure of vertebrate telomerase RNA", Cell, 100(5):503-514.

Crouse, J. and Amorese, D., (1987) "Ethanol Precipitation: Ammonium Acetate as an Alternative to Sodium Acetate", Focus, 9(2):3-5.

Damha, M. J. et al., (1990) "An improved procedure for derivatization of controlled-pore glass beads for solid-phase oligonucleotide synthesis", Nucleic Acids Research, 18(13):3813-3821.

Kim, M. M. et al., (2001) "A low threshold level of expression of mutant-template telomerase RNA inhibits human tumor cell proliferation", Proceedings of the National Academy of Sciences USA, 98(14):7982-7987.

Kupihar, Z. et al., (2001) "Synthesis and application of a novel, crystalline phosphoramidite monomer with thiol terminus, suitable for the synthesis of DNA conjugates", Bioorganic and Medicinal Chemistry Letters, 9(5):1241-1247.

Maskos, U. and Southern, E. M., (1992) "Oligonucleotide hybridisations on glass supports: a novel linker for oligonucleotide synthesis and hybridisation properties of oligonucleotides synthesised in situ", Nucleic Acids Research, 20(7):1679-1684.

Moore, D. and Dowhan, D. (2002) "Preparation and Analysis of DNA" in Current Protocols in Molecular Biology, John Wiley and Sons, Supplement 59, 2.1.1-2.1.10.

Ohtsuka, E. et al., (1982) "Recent developments in the chemical synthesis of polynucleotides", Nucleic Acids Research, 10(21):6553-6570.

Pruzan, R. et al., (2002) "Allosteric inhibitors of telomerase: oligonucleotide N3'->P5' phosphoramidates", Nucleic Acids Research, 30(2): 559-568.

Shea, R. G. et al., (1990) "Synthesis, hybridization properties and antiviral activity of lipid-oligodeoxynucleotide conjugates", Nucleic Acids Research, 18:3777-3783.

Uhlmann, E. and Peyman, A., (1990) "Antisense oligonucleotides: a new therapeutic principle", Chemical Reviews, 90 (4):543-584.

Gryaznov, S. M., (2010) "Oligonucleotide N3->P5 phosphoramidates and thio-phosphoramidates as potential therapeutic agents", Chemistry and Biodiversity, 7(3):477-493.

Sawadago, M. et al., (1991) "A rapid method for the purification of deprotected oligodeoxynucleotides", Nucleic Acids Research, 19(3):674.

Dong, G., (2003) "Solid-Phase Synthesis of Dipeptide-Conjugated Nucleosides and Their Interaction with RNA", Helvetica Chimica Acta, 86(10):3516-3524.

Goodnow, R. A., (1997) "Synthesis of thymine, cytosine, adenine, and guanine containing N-Fmoc protected amino acids: Building blocks for construction of novel oligonucleotide backbone analogs", Tetrahedron Letters, 38 (18):3195-3198.

(56) References Cited

OTHER PUBLICATIONS

Fields, G. B., (1994) "Peptide Synthesis Protocols", Methods in Molecular Biology, 35:17-27.

Demirtas, I., et al., (2002) "The Selective Protection and Deprotection of Ambident Nucleophiles with Parent and Substituted Triarylmethyls", Turkish Journal of Chemistry, 26:889-896.

Nelson, J. S. et al., (1997) "N3'->P5' Oligodeoxyribonucleotide Phosphoramidates: A New Method of Synthesis Based on a Phosphoramidite Amine-Exchange Reaction", Journal of Organic Chemistry, 62(21):7278-7287.

Cech, D. et al., (1996) "New Approaches Towards the Synthesis of Non-Radioactively Labelled Nucleoside Triphosphates as Terminators for DNA Sequencing", Collect. Czech. Chem. Commun., 61:S297-S300.

Chapuis, H. and Strazewski, P., (2006) "Shorter puromycin analog synthesis by means of an efficient Staudinger-Vilarrasa coupling", Tetrahedron, 62(51):12108-12115.

Kates, S. A. et al., (2000) "Solid-Phase Synthesis: A Practical Guide", Marcel-Dekker Inc., New York , 478-480.

Zaitseva, V. E. et al., (1984) Sov. J. Bioorg. Chem., 10(5):369-378 (translated from Bioorg. Khim, 10(5):670-680.

Amarnath, V. and Broom, A. D., (1977) "Chemical Synthesis of Oligonucleotides", Chemical Reviews, 77(2):183-217.

Beaucage, S. L. and Iyer, R. P., (1992) "Advances in the Synthesis of Oligonucleotides by the Phosphoramidite Approach", Tetrahedron, 48(12):2223-2311.

Brown, T. et al., (1989) "A new base-stable linker for solid-phase oligonucleotide synthesis", Journal of the Chemical Society, Chemical Communications, 14:891-893.

Chen, B. et al., (2013) "Evaluation of mobile phase composition for enhancing sensitivity of targeted quantification of oligonucleotides using ultra-high performance liquid chromatography and mass spectrometry: Application to phosphorothioate deoxyribonucleic acid", Journal of Chromatography A, 1288:73-91.

Iyer, R. P. et al., (1990) "The automated synthesis of sulfur-containing oligodeoxyribonucleotides using 3H-1,2-oenzodithiol-3-one 1,1-dioxide as a sulfur-transfer reagent", The Journal of Organic Chemistry, 55(15):4693-4699.

McCurdy, S. N. et al., (1997) "An improved method for the synthesis of N3'→P5' phosphoramidate oligonucleotides", Tetrahedron Letters, 38(2):207-210.

Mishra, R. K. et al., (1995) "Improved leishmanicidal effect of phosphorotioate antisense oligonucleotides by LDL-mediated delivery", Biochimica et Biophysica Acta, 1264(2):229-237.

Zimmermann, A. et al., (2014) "Synthetic oligonucleotide separations by mixed-mode reversed-phase/weak anion-exchange liquid chromatography", Journal of Chromatography A, 1354:43-55.

Ohkubo, A. et al., (2010) "Oligonucleotide Synthesis Involving Deprotection of Amidine-Type Protecting Groups for Nucleobases under Acidic Conditions", Organic Letters, 12(11):2496-2499.

Pon, R. T. et al., (1988) "Derivatization of controlled pore glass beads for solid phase oligonucleotide synthesis", Biotechniques, 6:768-775.

Pon, R. T. et al., (1993) "Solid-phase supports for oligonucleotide synthesis", in Agrawal, S., editor, Methods in Molecular Biology, 20:465-496.

Rump, E. T. et al., (1998) "Preparation of conjugates of oligodeoxynucleotides and lipid structures and their interaction with low-density lipoprotein", Bioconjugate Chemistry, 9:341-349.

Bastin, R. J. et al., (2000) "Salt Selection and Optimisation Procedures for Pharmaceutical New Chemical Entities", Organic Process Research and Development, American Chemical Society, 4(5):427-435.

METHODS OF POLYNUCLEOTIDE PREPARATION USING MULTIVALENT CATION SALT COMPOSITIONS

CROSS REFERENCE TO RELATED APPLICATION

Pursuant to 35 U.S.C. § 119(e), this application claims priority to the filing date of U.S. provisional application Ser. No. 62/151,891, filed Apr. 23, 2015, the disclosure of which is herein incorporated by reference.

INTRODUCTION

Nucleic acid polymer chemistry has played a role in many developing technologies in the pharmaceutical, diagnostic, and analytical fields, and more particularly in the subfields of antisense and anti-gene therapeutics, combinatorial chemistry, branched DNA signal amplification, and array-based DNA diagnostics and analysis. Some of this polymer chemistry has been directed to improving the binding strength, specificity, and nuclease resistance of natural nucleic acid polymers, such as DNA. Peptide nucleic acid (PNAs), phosphorothioate, methylphosphonate and phosphoramidate internucleoside linkages are examples of some polymer chemistries that have been applied to polynucleotides to provide for one or more desirable properties such as nuclease resistance, cellular uptake and solubility.

Polynucleotide N3'→P5' phosphoramidates can form stable duplexes with complementary DNA and RNA strands, as well as stable triplexes with DNA duplexes, and are resistant to nucleases. Polynucleotide N3'→P5' thiophosphoramidates have found use as potent antisense agents both in vitro and in vivo. Polynucleotide containing compounds that inhibit telomerase activity can be used to treat telomerase-mediated disorders, such as cancer, since cancer cells express telomerase activity and normal human somatic cells do not possess telomerase activity at biologically relevant levels. As such, methods of preparing and isolating such polynucleotides are of interest.

SUMMARY

Aspects of the disclosure include methods for the preparation of a polynucleotide. In some embodiments, the method includes contacting a first polynucleotide composition including: a polynucleotide having a sequence of 7 or more nucleoside subunits where at least two of the nucleoside subunits are joined by a N3'→P5' thiophosphoramidate inter-subunit linkage; and non-target synthetic products and reagents; with a multivalent cation salt to precipitate a first polynucleotide salt including at least one multivalent cation counterion; and separating the polynucleotide salt from the contacted first polynucleotide composition to produce a second polynucleotide composition including the first polynucleotide salt. In certain embodiments, the method further includes contacting the first polynucleotide salt with a reverse phase chromatography support; and eluting from the chromatography support a third polynucleotide composition including a second polynucleotide salt. Also provided are compositions including a salt of the polynucleotide including at least one multivalent cation counterion. In some embodiments, the at least one multivalent cation counterion is selected from the group consisting of magnesium, zinc, aluminium, and calcium.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
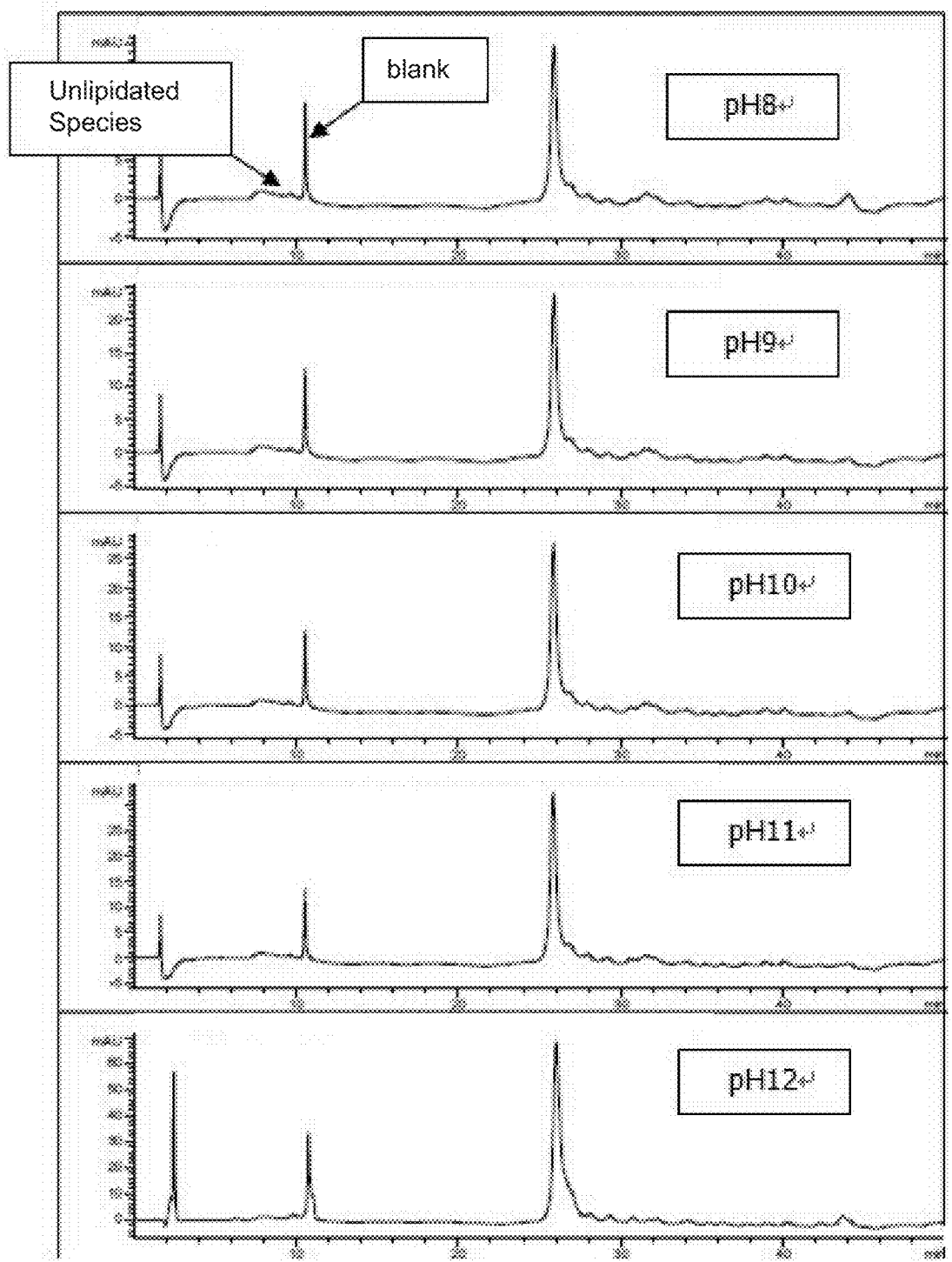
FIG. 1 shows HPLC chromatograms of Imetelstat-Mg in 1M NaCl solutions at a variety of pH's.

Before describing exemplary embodiments in greater detail, the following definitions are set forth to illustrate and define the meaning and scope of the terms used in the description.

The following terms have the following meanings unless otherwise indicated. Any undefined terms have their art recognized meanings.

As used herein, the terms polynucleotide and oligonucleotide are used interchangeably to refer to a compound containing a plurality of nucleoside moiety subunits or nucleoside residues that are linked by internucleoside bonds or internucleosidic linkages. Whenever a polynucleotide is represented by a sequence of letters, such as "ATGUCCTG," it is understood that the nucleotides are in 5'→3' order from left to right and that "A" denotes deoxyadenosine, "C" denotes deoxycytidine, "G" denotes deoxyguanosine, "T" denotes thymidine, and "U" denotes deoxyuridine, unless otherwise noted.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described generally by Scheit, Nucleotide Analogs (John Wiley, New York, 1980). Such analogs include synthetic nucleosides designed to enhance binding properties, e.g. stability, specificity, or the like, such as disclosed by Uhlmann and Peyman (Chemical Reviews, 90:543-584, 1990). In some embodiments, a nucleoside or nucleoside analog includes a 3'-hydroxyl group or a 3'-amino group.

The terms "base" and "nucleobase" are used interchangeably and defined herein to include (i) conventional DNA and RNA bases (uracil, thymine, adenine, guanine, and cytosine), and (ii) modified bases or base analogs (e.g., 5-methyl-cytosine, 5-bromouracil, or inosine). A base analog is a chemical whose molecular structure mimics that of a conventional DNA or RNA base.

As used herein, "pyrimidine" means the pyrimidines occurring in natural nucleosides, including cytosine, thymine, and uracil, and common analogs thereof, such as those containing oxy, methyl, propynyl, methoxy, hydroxyl, amino, thio, halo, and like, substituents. The term as used herein further includes pyrimidines with common protecting groups attached, such as N4-benzoylcytosine. Further pyrimidine protecting groups of interest include but are not limited to, those protecting groups are disclosed by Beaucage and Iyer Tetrahedron 48: 2223-2311 (1992).

As used herein, "purine" means the purines occurring in natural nucleosides, including adenine, guanine, and hypoxanthine, and common analogs thereof, such as those containing oxy, methyl, propynyl, methoxy, hydroxyl, amino, thio, halo, and like, substituents. The term as used herein further includes purines with common protection groups attached, such as N2-benzoylguanine, N2-isobutyrylguanine, N6-benzoyladenine, and the like. Further common purine protection groups are disclosed by Beaucage and Iyer Tetrahedron 48: 2223-2311 (1992). As used herein, the term "-protected-" as a component of a chemical name refers to art-recognized protection groups for a particular moiety of a compound, e.g. "5'-protected-hydroxyl" in reference to a nucleoside includes triphenylmethyl (i.e., trityl), p-anisyldiphenylmethyl (i.e., monomethoxytrityl or MMT), di-p-anisylphenylmethyl (i.e., dimethoxytrityl or DMT), and the like; and a protected nucleobase in reference to a nucleobase including a heteroatom protected with a group such as a dimethylaminoformamidine (DMF), benzoyl (Bz), isobutyryl, and the like. Art-recognized protecting groups include those described in the following references: Gait, editor, Oligonucleotide Synthesis: A Practical Approach (IRL Press, Oxford, 1984); Amarnath and Broom, Chemical Reviews, 77:183-217, 1977; Pon et al., Biotechniques, 6:768-775, 1988; Ohtsuka et al., Nucleic Acids Research, 10:6553-6570, 1982; Eckstein, editor, Oligonucleotides. and Analogues: A Practical Approach (IRL Press, Oxford, 1991), Greene and Wuts, Protective Groups in Organic Synthesis, Second Edition, (John Wiley & Sons, New York, 1991), Narang, editor, Synthesis and Applications of DNA and RNA (Academic Press, New York, 1987), Beaucage and Iyer Tetrahedron 48: 2223-2311 (1992), and like references.

As used herein, "polynucleotide N3'→P5' thiophosphoramidate" means an oligomer, usually linear, of nucleoside subunits linked by at least one N3'→P5' thiophosphoramidate linkage. In general terms, the nucleoside subunits comprise nucleosides or nucleoside analogs, but may also comprise more general moieties having compatible chemistry, such as abasic sugars and other hydrocarbon moieties, such as described in the following references: Newton et al., Nucleic Acids Research, 21: 1155-1162 (1993); Griffin et al., J. Am. Chem. Soc., 114: 7976-7982 (1992); Jaschke et al., Tetrahedron Letters, 34: 301-304 (1992); Ma et al., International application PCT/CA92/00423; Zon et al., International application PCT/US90/06630; Durand et al., Nucleic Acids Research, 18: 6353-6359 (1990); Salunkhe et al., J. Am. Chem. Soc., 114: 8768-8772 (1992); and the like. In some instances, the term means a polynucleotide where all internucleosidic linkages are replaced by N3'→P5' thiophosphoramidate linkages. As such, the term comprehends partially as well as fully "amidated" oligomers. In some instances, the term means a polynucleotide where all the internucleosidic linkages are replaced by N3'→P5' thiophosphoramidate linkages and wherein the nucleoside subunits are the natural nucleosides or analogs thereof. A subject polynucleotide N3'→P5' thiophosphoramidate in which every linkage is an N3'→P5' thiophosphoramidate linkage ("fully amidated") may be imbedded in or attached to other oligonucleotides or polynucleotides to form a larger oligomer which is "partially amidated." A subject polynucleotide N3'→P5' thiophosphoramidate may include any convenient 3' and/or 5' terminal groups. In some embodiments, the polynucleotide N3'→P5' thiophosphoramidate includes a 3'-hydroxyl terminal group or a 3'-amino terminal group.

As used herein, the terms "phosphate" and "phosphate group" are meant to encompass a thiophosphate group and an oxophosphate group.

As used herein, the term "phosphoramidite amino group" refers to the amino group, $-NR^4R^5$, attached to the phosphorus atom of a phosphoramidite group, and the term "phosphoramidite nitrogen" refers to the nitrogen atom of the phosphoramidite amino group.

"Alkyl" refers to monovalent saturated aliphatic hydrocarbyl groups having from 1 to 10 carbon atoms and such as 1 to 6 carbon atoms (e.g., "an alkyl of 1 to 6 carbons atoms"), or 1 to 5 (e.g., "an alkyl of 1 to 5 carbons atoms"), or 1 to 4 (e.g., "an alkyl of 1 to 4 carbons atoms"), or 1 to 3 carbon atoms (e.g., "an alkyl of 1 to 3 carbons atoms").

This term includes, by way of example, linear and branched hydrocarbyl groups such as methyl ($CH_3-$), ethyl ($CH_3CH_2-$), n-propyl ($CH_3CH_2CH_2-$), isopropyl (($CH_3)_2CH-$), n-butyl ($CH_3CH_2CH_2CH_2-$), isobutyl (($CH_3)_2CHCH_2-$), sec-butyl (($CH_3)(CH_3CH_2)CH-$), t-butyl (($CH_3)_3C-$), n-pentyl ($CH_3CH_2CH_2CH_2CH_2-$), and neopentyl (($CH_3)_3CCH_2-$).

The term "substituted alkyl" refers to an alkyl group as defined herein wherein one or more carbon atoms in the alkyl chain have been optionally replaced with a heteroatom such as $-O-$, $-N-$, $-S-$, $-S(O)_n-$ (where n is 0 to 2), $-NR-$ (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, $-SO$-alkyl, $-SO$-aryl, $-SO$-heteroaryl, $-SO_2$-alkyl, $-SO_2$-aryl, $-SO_2-$ heteroaryl, and $-NR^aR^b$, wherein $R^a$ and $R^b$ may be the same or different and are chosen from hydrogen, optionally substituted alkyl, cycloalkyl, alkenyl, cycloalkenyl, alkynyl, aryl, heteroaryl and heterocyclic. In some instances, a "substituted alkyl" refers to an alkyl group as defined herein having from 1 to 5 substituents selected from the group consisting of alkoxy, cycloalkyl, cycloalkenyl, acyl, acylamino, acyloxy, amino, aminoacyl, aminoacyloxy, oxyaminoacyl, azido, cyano, halogen, hydroxyl, carboxyl, carboxylalkyl, thiol, thioalkoxy, aryl, aryloxy, heteroaryl, heteroaryloxy, heterocyclyl, heterocyclooxy, sulfonamido, and $-NR^aR^b$, wherein $R^a$ and $R^b$ may be the same or different and are chosen from hydrogen, alkyl, cycloalkyl, alkenyl, cycloalkenyl, alkynyl, aryl, heteroaryl and heterocyclic.

"Alkoxy" refers to the group $-O$-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)-$ The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$— heteroaryl, and trihalomethyl. In such cases, a heteroaryl group that is substituted with from 1 to 5 substituents (e.g., as described herein) is referred to as a "substituted heteroaryl".

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$-moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Nitro" refers to the group —NO$_2$.

"Oxo" refers to the atom (=O).

"Thiol" refers to the group —SH.

"Thioxo" or the term "thioketo" refers to the atom (=S).

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, and the like; and when the molecule contains a basic functionality, salts of organic or inorganic acids, such as hydrochloride, and the like. Pharmaceutically acceptable salts of interest include, but are not limited to, aluminium, ammonium, arginine, barium, benzathine, calcium, cholinate, ethylenediamine, lysine, lithium, magnesium, meglumine, procaine, potassium, sodium, tromethamine, N-methylglucamine, N,N'-dibenzylethylene-diamine, chloroprocaine, diethanolamine, ethanolamine, piperazine, zinc, diisopropylamine, triethylamine, diisopropylethylamine and triethanolamine salts.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt. Salts of interest include, but are not limited to, aluminium, ammonium, arginine, barium, benzathine, calcium, cesium, cholinate, ethylenediamine, lithium, magnesium, meglumine, procaine, N-methylglucamine, piperazine, potassium, sodium, tromethamine, zinc, N,N'-dibenzylethylene-diamine, chloroprocaine, diethanolamine, ethanolamine, piperazine, diisopropylamine, triethylamine, diisopropylethylamine and triethanolamine salts. It is understood that for any of the polynucleotide structures depicted herein that include a backbone of internucleoside linkages, such polynucleotides may also include any convenient salt forms. In some embodiments, acidic forms of the internucleoside linkages are depicted for simplicity. In some instances, the salt of the subject compound is a monovalent cation salt. In certain instances, the salt of the subject compound is a divalent cation salt. In some instances, the salt of the subject compound is a trivalent cation salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, —NH—P(=S)(OH)—O— and —NH—P(=O)(SH)—O—, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric arrangements of the groups described herein are possible. For example, it is understood that a polynucleotide described by the following structure:

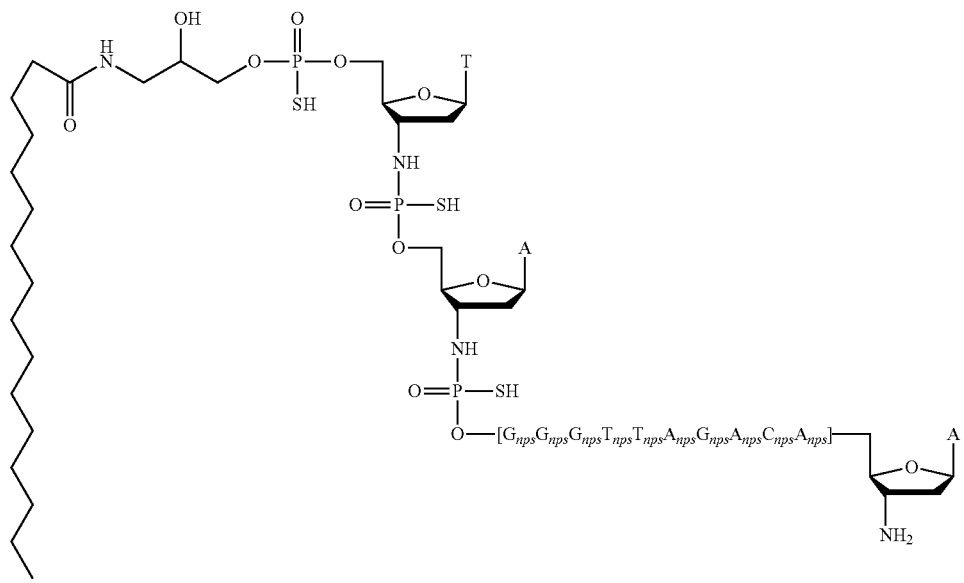

also encompasses the following structure showing one possible alternate tautomeric arrangement of linkage groups:

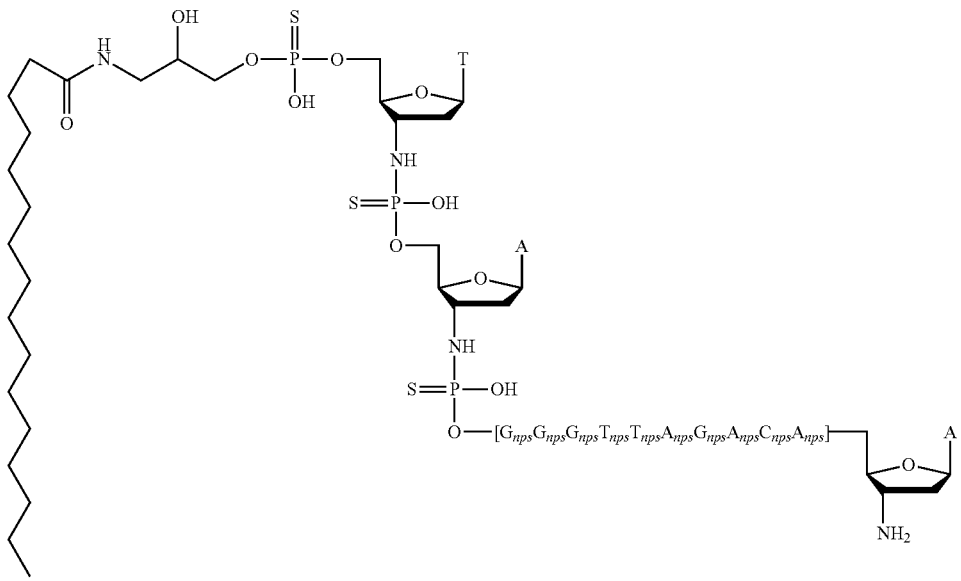

where "nps" represents a thiophosphoramidate linkage (—NH—P(=O)(SH)—O— or —NH—P(=S)(OH)—O—) connecting the 3'-carbon of one nucleoside to the 5'-carbon of the adjacent nucleoside. It is understood that all tautomeric forms of a subject compound are encompassed by a structure where one possible tautomeric arrangement of the groups of the compound is described, even if not specifically indicated. Any convenient tautomeric arrangement of the groups of the subject compounds may be utilized in describing the compounds.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound. It is understood that the term "or a salt thereof" is intended to include all permutations of salts. It is understood that the term "or a pharmaceutically acceptable salt thereof" is intended to include all permutations of salts. It is understood that the term "or a solvate thereof" is intended to include all permutations of solvates. It is understood that the term "or a stereoisomer thereof" is intended to include all permutations of stereoisomers. It is understood that the term "or a tautomer thereof" is intended to include all permutations of tautomers. Thus for example it follows that it is intended to include a solvate of a pharmaceutically acceptable salt of a tautomer of a stereoisomer of subject compound.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 81% free, at least 82% free, at least 83% free, at least 84% free, at least 85% free, at least 86% free, at least 87% free, at least 88% free, at least 89% free, at least 90% free, at least 91% free, at least 92% free, at least 93% free, at least 94% free, at least 95% free, at least 96% free, at least 97% free, at least 98% free, at least 99% free, or more than 99% free, from other components with which it is naturally associated.

The term "physiological conditions" is meant to encompass those conditions compatible with living cells, e.g., predominantly aqueous conditions of a temperature, pH, salinity, etc. that are compatible with living cells.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Other definitions of terms may appear throughout the specification.

DESCRIPTION OF EXEMPLARY EMBODIMENTS

As summarized above, aspects of the disclosure include methods for the preparation of a polynucleotide. In some embodiments, the method includes contacting a first polynucleotide composition including: a polynucleotide having a sequence of 7 or more nucleoside subunits where at least two of the nucleoside subunits are joined by a N3'→P5' thiophosphoramidate inter-subunit linkage; and non-target synthetic products and reagents; with a multivalent cation salt to precipitate a first polynucleotide salt including at least one multivalent cation counterion; and separating the first polynucleotide salt from the contacted first polynucleotide composition to produce a second polynucleotide composition including the first polynucleotide salt. In certain embodiments, the method further includes contacting the polynucleotide salt with a reverse phase chromatography support; and eluting from the chromatography support a third polynucleotide composition including the polynucleotide. In some instances, third polynucleotide composition includes a second polynucleotide salt. Also provided are compositions including a salt of the polynucleotide including at least one multivalent cation counterion. In some embodiments, the at least one multivalent cation counterion is selected from the group consisting of magnesium, zinc, aluminium, and calcium.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, methods and materials of interest are now described. All publications mentioned herein are incorporated herein by reference to disclose and describe the methods and/or materials in connection with which the publications are cited.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

All patents and publications, including all sequences disclosed within such patents and publications, referred to herein are expressly incorporated by reference.

In further describing the subject invention, methods of preparing a polynucleotide are described first in greater detail. Next, polynucleotide compositions of interest for practicing the subject methods are reviewed.

Methods of Preparation

Aspects of the present disclosure include methods for the preparation of a polynucleotide. In some embodiments, the method includes contacting a first polynucleotide composition including a polynucleotide (e.g., as described herein) and non-target synthesis products and agents, with a multivalent cation salt to precipitate a polynucleotide salt including at least one multivalent cation counterion. Precipitation of the polynucleotide salt using the subject methods provides for removal of all soluble non-target synthesis products and agents. In some embodiments, the method includes separating the polynucleotide salt from the contacted first polynucleotide composition to produce a second polynucleotide composition including the polynucleotide salt. In certain embodiments, the first polynucleotide composition, the polynucleotide salt and the second polynucleotide composition each include a target polynucleotide having a sequence of 7 or more nucleoside subunits where at least two of the nucleoside subunits are joined by a N3'→P5' thiophosphoramidate inter-subunit linkage (e.g., as described herein).

The second polynucleotide composition may have a reduced amount of non-target synthesis products and agents as compared to the first polynucleotide composition. By reduced amount of non-target synthesis products and agents is meant that there is a 10% or more by weight reduction of the non-target synthesis products and agents in the second polynucleotide composition as compared to the first polynucleotide composition, such as a 15% or more by weight reduction, 20% or more by weight reduction, 25% or more by weight reduction, 30% or more by weight reduction, 35% or more by weight reduction, 40% or more by weight reduction, 45% or more by weight reduction, 50% or more by weight reduction, 55% or more by weight reduction, 60% or more by weight reduction, 65% or more by weight reduction, 70% or more by weight reduction, 75% or more by weight reduction, 80% or more by weight reduction, 85% or more by weight reduction, 90% or more by weight reduction, or 95% or more by weight reduction. As such, the subject methods may provide for selective precipitation of target polynucleotide over non-target synthesis products and agent. In certain embodiments, the subject methods provide for improved selectivity of precipitation as compared to a control method of polynucleotide precipitation using an organic solvent, such as neat ethanol or an ethanol solution (see e.g., Crouse J, Amorese D (1987). "Ethanol Precipitation: Ammonium Acetate as an Alternative to Sodium Acetate". Focus 9 (2): 3-5). By improved selectivity of precipitation is meant that 5% or more by weight of non-target synthesis products and agents are removed from the second polynucleotide composition as compared to a control composition, such as 10% or more by weight, 15% or more by weight, 20% or more by weight, 25% or more by weight, 30% or more by weight, 35% or more by weight, 40% or more by weight, 45% or more by weight, 50% or more by weight, 55% or more by weight, 60% or more by weight, 65% or more by weight, 70% or more by weight, 75% or more by weight, 80% or more by weight, 85% or more by weight, 90% or more by weight, or 95% or more by weight of non-target synthesis products and agents are removed. The reduced amount of non-target synthesis products and agents as compared to the first polynucleotide composition may be determined using any convenient methods, for example using HPLC methods.

As used herein, the terms "target synthetic polynucleotide" and "target polynucleotide" are used interchangeably and refer to a polynucleotide having a particular desired sequence of nucleotides that is synthesized on a support via any convenient stepwise solid phase polynucleotide synthesis method (e.g., as described herein), and where the polynucleotide is devoid of any protecting groups that are utilized solely for purposes of executing the synthetic strategy of the target polynucleotide. Such protecting groups may be removed from a polynucleotide in the final steps of solid phase synthesis, e.g., during final deprotection and cleavage of the polynucleotide from a support to produce the target polynucleotide. As used herein, the term "non-target" refers to any convenient component, e.g., a compound, a polynucleotide or derivative thereof, an agent, etc., or mixtures thereof that is not the desired target product of a synthesis.

The target polynucleotide can include any convenient number of nucleoside subunits, such as between 7 and 500 nucleoside subunits, between 7 and 100 nucleoside subunits, between 7 and 75 nucleoside subunits, between 7 and 50 nucleoside subunits, between 7 and 40 nucleoside subunits, between 7 and 30 nucleoside subunits, between 7 and 20 nucleoside subunits, between 7 and 15 nucleoside subunits, between 10 and 15 nucleoside subunits, or between 13 and 15 nucleoside subunits. In some instances, the target polynucleotide has between 7 and 100 nucleoside subunits, such as between 7 and 50 nucleoside subunits, between 10 and 50 nucleoside subunits, between 10 and 40 nucleoside subunits, between 10 and 30 nucleoside subunits, between 10 and 25 nucleoside subunits, between 10 and 20 nucleoside subunits, between 12 and 18 nucleoside subunits, or between 12 and 16 nucleoside subunits. In certain cases, the target polynucleotide has 7, 8, 9, 10, 11, 12, 13, 14, 15, 16, 17, 18, 19, 20, 21, 22, 23, 24 or 25 nucleoside subunits.

As used herein, the term "non-target synthesis products and agents" refers collectively to a variety of non-target components that may be present in a crude synthetic product of solid phase polynucleotide synthesis, including but not limited to: non-target polynucleotide products of the synthesis, such as truncated polynucleotides, capped polynucleotide fragments (i.e., sequences that were capped after a failed subunit coupling), polynucleotides including deletion(s) (i.e., missing one or more target nucleoside monomers or dimers, e.g., as described herein) and derivatized polynucleotides (e.g., polynucleotide sequences that undergo an undesirable side reaction during synthesis or cleavage); and agents such as cleaved linkers, products of deprotection, e.g., removed protecting group products such as phosphorus protecting groups products and base protecting group products (e.g., exocyclic amine protecting group products), cleavage reagents and/or cleavage scavengers and residual synthesis reagents, such as monomers, dimers, coupling, capping or deprotection reagents.

In certain embodiments, the methods provide for selective precipitation of target polynucleotide over non-target synthesis products and agents that include polynucleotides having 6 nucleoside subunits or less, such as 5 or less, 4 or less, 3 or less or 2 nucleoside subunits. In certain cases, all non-target synthesis products and agents which are not polynucleotides remain soluble during the selective precipitation step of the subject methods and may thus be easily removed from the resulting polynucleotide salt precipitate.

The subject methods may include precipitation and separation of the target polynucleotide from a crude synthetic preparation to produce a polynucleotide composition that has several desirable properties, such as a reduced amount of non-target synthesis products and agents (e.g., synthesis reagents, cleavage reagents, scavengers, removed protecting groups, cleavage side products (linkers, capping groups, etc.), and small polynucleotide fragments).

In some embodiments, the subject methods include precipitating the polynucleotide from a crude synthetic preparation as a multivalent cation salt prior to chromatography purification. In certain cases, the subject methods are methods of purification of a target polynucleotide. Precipitation of the crude polynucleotide composition using a multivalent cation salt produces a polynucleotide salt precipitate including at least one multivalent cation counterion. In some cases, the polynucleotide salt precipitate includes a mixture of monovalent and multivalent cation counterions which form ion pairs with the polyanionic polynucleotide backbone. As used here, the terms "multivalent cation salt" and "multivalent salt" when used in reference to a polynucleotide are used interchangeably to refer to a polynucleotide salt that includes at least one multivalent cation counterion that is ion paired to an anionic inter-subunit linkage group of the polynucleotide backbone. In some instances, the multivalent cation salt of the polynucleotide includes a mixture of monovalent and multivalent cations. In some embodiments, the multivalent cation may provide for aggregation of the target polynucleotide by ion pairing to anionic inter-subunit linkage groups of two or more polynucleotide backbones. In certain instances, a divalent cation ion pairs with two distinct polynucleotides to form a dimer. In some cases, further aggregation of the polynucleotides may be achieved by additional multivalent interactions mediated by additional multivalent cations. As such, in some cases, the subject methods may provide for selective aggregation and precipitation of target polynucleotides over non-target synthetic products and agents.

In some embodiments of the method, the at least one multivalent cation counterion is divalent. In certain embodiments, the at least one multivalent cation counterion is selected from the group consisting of magnesium, zinc and calcium. In some embodiments, the at least one multivalent cation counterion is trivalent. In certain embodiments, the at least one multivalent cation counterion is aluminium. In some embodiments, the polynucleotide salt further includes a monovalent cation counterion. In such cases, the polynucleotide salt is a mixed salt, e.g., a salt including two or more different cation counterions.

Any convenient methods of precipitating a polynucleotide may find use in the subject methods. The step of contacting the first polynucleotide composition with a multivalent cation salt to precipitate a polynucleotide salt including at least one multivalent cation counterion may be achieved using any convenient methods. Any convenient multivalent cations and salts thereof (e.g., as described herein) may be utilized in the contacting step to produce the precipitate. In certain instances, a salt of a polynucleotide including at least one multivalent cation counterion is produced in a solution phase, e.g., via the addition of a multivalent cation salt to a solution including the polynucleotide. Once the multivalent cation salt has been added to the solution the precipitate may then form. In some cases, a salt of a polynucleotide including at least one multivalent cation counterion may be formed on an ion exchange support. Any convenient ion exchange supports may be utilized in the contacting step. In some cases, the ion exchange support is a strong cation exchange resin. In some embodiments of the method, the contacting step includes eluting the first polynucleotide composition from a cation exchange support that includes multivalent cation counterions. As used herein, the term "cation exchange support" refers to a support which is itself anionic and is capable of ion pairing with a cationic analyte, such as a multivalent cation of interest. Any convenient eluant may be utilized for the step of eluting from the cation exchange support. In some instances, the precipitate forms in the eluate after the polynucleotide salt has been eluted from the cation exchange support.

The subject methods may be performed on any convenient crude synthetic preparation of a target synthetic polynucleotide. In some instances, the first polynucleotide composition is a crude synthetic preparation of a target synthetic polynucleotide. In certain embodiments, the first polynucleotide composition is a composition that is the product of cleavage of a target polynucleotide from a support, post synthesis. As such, the first polynucleotide composition may include a variety of non-target synthetic products and agents. The subject methods provide for selective precipitation of the polynucleotide salt over non-target synthesis products and agents, which remain in solution and thus can be easily removed from the resulting precipitate.

Any convenient methods of synthesis (e.g., as described herein) may be utilized to synthesize the target polynucleotide. Following synthesis, the target polynucleotide is cleaved from the support on which stepwise synthesis is performed. Following cleavage, the full length target polynucleotide may be purified to remove undesirable synthesis and cleavage reagents and to remove non-target polynucleotide fragments, and derivatives thereof. The subject methods including precipitation of the polynucleotide salt including at least one multivalent cation counterion may be performed at any convenient stage of the preparation of a target polynucleotide, such as post synthesis and prior to reverse phase chromatography purification.

As used herein, the terms "crude synthetic preparation", "crude composition" and "crude polynucleotide" refer to a composition including the synthetic products of solid phase polynucleotide synthesis that are collected post synthesis via cleavage from a solid phase synthesis support, where the composition is unpurified, i.e., no chromatography purification has been performed on the composition. Chromatography purification refers to any convenient purification method that includes absorption of target polynucleotide to a chromatography support and subsequent elution and resolution of the target polynucleotide from non-target polynucleotides. In some cases, chromatography purification refers to reverse phase chromatography purification.

In some embodiments, the method further includes providing a first polynucleotide composition, where the composition is produced via post synthesis cleavage from a solid phase synthesis support. Any convenient additional steps such as evaporation, dilution, or concentration steps may also be performed on the crude synthetic preparation prior to utilizing the resulting composition in the subject methods. In some instances, the method further includes synthesizing the target polynucleotide (e.g., as described herein on a solid phase synthesis support). In certain embodiments, the method further includes cleaving the polynucleotide from a support to produce the first polynucleotide composition.

A solid precipitate including the polynucleotide salt may be separated from the first polynucleotide composition that is contacted with the multivalent salt (i.e., the contacted first polynucleotide composition) using any convenient method. Separation methods of interest include, but are not limited to, centrifugation, filtration, decanting, and the like.

In some instances, separation of the precipitate including the polynucleotide salt is achieved by centrifugation where the application of a centrifugal force to the contacted first polynucleotide composition, e.g., in a centrifuge, causes the precipitate to form a pellet, e.g., at the bottom of the container. The formation of a pellet via centrifugation may be referred to as spinning down the precipitate. In certain embodiments of the method, the separating step includes centrifuging the contacted first polynucleotide composition to spin down the polynucleotide salt precipitate. The supernatant liquid may then be decanted from the tube without disturbing the precipitate, or withdrawn from the container, e.g., with a Pasteur pipette. The centrifugation process can be repeated with a wash solution.

In some instances, separation of the precipitate including the polynucleotide salt is achieved by filtration. In some embodiments of the method, the separating step includes filtering the polynucleotide salt from the contacted first polynucleotide. Any convenient filters and filter media may be utilized in the subject methods. In certain cases, the separation is achieved by depth filtration using a filter media that is selected according to the target polynucleotide.

In some embodiments, the method includes: contacting a first polynucleotide composition including: a polynucleotide having a sequence of 7 or more nucleoside subunits and at least two of the nucleoside subunits are joined by a N3'→P5' thiophosphoramidate inter-subunit linkage; and non-target synthetic products and agents;
with a multivalent cation salt to precipitate a first polynucleotide salt including at least one multivalent cation counterion; and
separating the first polynucleotide salt from the contacted first polynucleotide composition to produce a second polynucleotide composition including the polynucleotide salt.

Separating the precipitate from the contacted first polynucleotide composition produces a second polynucleotide composition including the first polynucleotide salt. In some cases, selective precipitation of the first polynucleotide salt using the multivalent cation salt via the subject methods produces a second polynucleotide composition that includes a reduced amount of non-target synthetic products and agents.

After selective precipitation, the subject polynucleotide salts may then be converted into a soluble polynucleotide salt by cation exchange of the at least one multivalent cation counterion away from the polynucleotide and replacement with another cation counterion of interest (e.g., as described herein). As such, the subject methods provide for reversible formation of a first polynucleotide salt including at least one multivalent cation counterion. As used herein, the terms "reversible formation" and "reversible exchange" are used interchangeably and refer to the preparation of a polynucleotide salt by, e.g., selective precipitation (e.g., as described herein), where the salt formed may also be subsequently dissociated to exchange away the at least one multivalent cation salt from the salt. In some cases, polynucleotide salts which are insoluble in any solvent may be referred to as irreversibly formed salts. In some embodiments, the method includes exchanging the at least one multivalent cation counterion away from the first polynucleotide salt to produce a soluble second polynucleotide salt, where the exchanging includes dissociating the multivalent cation counterion and ion pairing with a soluble salt cation of interest. In certain instances, the soluble second polynucleotide salt is a monovalent salt. In certain instances, the soluble second polynucleotide salt is a sodium salt. In certain instances, the soluble second polynucleotide salt is a triethylammonium salt. In some instances, the first and second polynucleotide are distinct from each other, i.e., include different cation counterions. The dissociation of the subject polynucleotide salts and exchange of the at least one multivalent cation counterion may be achieved using any convenient methods. In certain instances, dissociation is achieved using reverse phase chromatography, e.g., as described herein. In some cases, ion exchange chromatography may be utilized to achieve dissociation. In certain embodiments, dissociation of the first polynucleotide salt is achieved by dissolution of the salt in a solvent including a cation counterion of interest.

After the separation, further purification steps may be performed on the second polynucleotide composition. In some embodiments, the method further includes: contacting the first polynucleotide salt with a reverse phase chromatography support; and eluting from the chromatography support a third polynucleotide composition including the polynucleotide. In certain embodiments, the third polynucleotide composition includes a second polynucleotide salt. Any convenient reverse phase chromatography methods may be utilized to purify the polynucleotide salt. Reverse phase chromatography methods and supports of interest include, but are not limited to, chromatographic purification using ion-pair reversed-phase chromatography, C18 reversed-phase chromatography and those methods and supports described by Chen et al., Journal of Chromatography A, Volume 1288, 3 May 2013, Pages 73-81; and Zimmermann et al., Journal of Chromatography A, Volume 1354, 8 Aug. 2014, Pages 43-55. In some embodiments, the second polynucleotide composition is loaded directly onto the reverse phase chromatography support. By loaded directly on the support is meant that the second polynucleotide composition produced using the subject method is added directly, e.g., as an isolated solid precipitate, to the reverse phase chromatography support. In some instances, the reverse phase chromatography support is a resin configured as a column and the polynucleotide composition is added to the top of the resin bed. In certain embodiments, the method further includes dissolving the second polynucleotide composition in a solvent. Any convenient solvents may be utilized, including but not limited to, aqueous buffers, organic solvents miscible with water and mixtures thereof. In such cases, a solution of the second polynucleotide composition may be contacted with the reverse phase chromatography support to absorb the polynucleotide to the support prior to elution.

In some cases, the contacting includes absorbing the polynucleotide onto the reverse phase chromatography support and subsequently eluting the polynucleotide to provide for chromatographic resolution of the target polynucleotide from non-target polynucleotide and residual synthetic agents that are present in the composition. The eluate containing target polynucleotide is collected. Any convenient eluants may be utilized to elute the polynucleotide from the reverse phase chromatography support. The eluant may be selected according to a variety of factors, such as the nature of the reverse phase chromatography support, the target oligonucleotide, particular desired salts of the target polynucleotide, etc. In some instances, the at least one multivalent cation counterion of the first polynucleotide salt is ion exchanged on the reverse phase chromatography support with another distinct cation counterion of interest that is included in the eluant. In such cases, when the polynucleotide is eluted from the reverse phase chromatography support, it is in a different salt form (i.e., a second polynucleotide salt) that when it was loaded because the at least one multivalent cation counterion is been exchanged away from the polynucleotide. In certain instances, the salt form of the polynucleotide that is eluted from the support in the third polynucleotide composition is more water soluble than the first polynucleotide salt including at least one multivalent cation counterion.

In certain embodiments, the third polynucleotide composition includes a second polynucleotide salt that is a pharmaceutically acceptable salt of the polynucleotide. In certain instances, the third composition includes a second polynucleotide salt that is a monovalent cation salt of the polynucleotide. In certain cases, the third composition includes a second polynucleotide salt that is a triethylammonium salt of the polynucleotide. In certain cases, the third composition includes a second polynucleotide salt that is a sodium salt of the polynucleotide. It is understood that after the polynucleotide is purified by reverse phase chromatography, any number of further cation counterion exchange steps may be performed on the polynucleotide salt to produce a desired salt form of the polynucleotide. In some embodiments, the method further includes ion exchanging cation counterions from the second polynucleotide salt to produce a third polynucleotide salt. In certain embodiments, the third polynucleotide salt is a pharmaceutically acceptable salt of the polynucleotide. In certain instances, the third polynucleotide salt is a monovalent cation salt of the polynucleotide. In certain instances, the third polynucleotide salt is a sodium salt of the polynucleotide (e.g., as described herein).

In certain instances, the first composition includes a monovalent cation salt of the polynucleotide. In certain cases, the monovalent cation salt is selected from the group consisting of sodium, ammonium and alkyl ammonium. In certain instances, the alkyl ammonium is selected from the group consisting of dimethylammonium, methylammonium, ethylammonium and triethylammonium. In certain cases, the first composition includes an ammonium salt of the polynucleotide. In certain cases, the first composition includes an alkyl ammonium salt of the polynucleotide. In certain cases, the first composition includes a triethylammonium salt of the polynucleotide. In certain cases, the first composition includes a sodium salt of the polynucleotide. The first polynucleotide composition may be contacted with a multivalent cation salt to precipitate a first polynucleotide salt including at least one multivalent cation counterion. As such, in certain embodiments, the contacted first polynucleotide composition includes the first polynucleotide salt including at least one multivalent cation counterion.

Considered to be embraced within the scope of this invention are embodiments of any of the above-indicated embodiments of the method, where the polynucleotide is as described herein.

Methods of Synthesis

Any convenient polynucleotide synthesis methods, strategies and chemistries may be utilized to prepare the crude synthetic product polynucleotide compositions which find use in the subject methods of preparation. Polynucleotide synthesis chemistries and methods of interest that may be adapted for use in the subject methods include, but are not limited to, phosphoramidite, H-phosphonate, phosphodiester, phosphotriester, phosphite triester. The polynucleotide components of the invention compounds may be synthesized by adapting any conventional protocols for the type of chemistry selected. Methods of interest for the synthesis of oligonucleotides having N3'→P5' thiophosphoramidate chemistries include, but are not limited to, those methods described in U.S. Pat. No. 5,824,793, McCurdy et al., (1997) Tetrahedron Letters, 38:207-210; Pongracz & Gryaznov, (1999) Tetrahedron Letters, 49:7661-7664; U.S. Pat. Nos. 6,835,826, 7,494,982, 7,485,717 and 5,684,143.

In some cases, a polynucleotide of interest is synthesized via sequential couplings starting from the 5'-terminal and proceeding to the 3'-terminal of the target polynucleotide sequence. In certain cases, a polynucleotide of interest is synthesized via sequential couplings starting from the 3'-terminal and proceeding to the 5'-terminal of the target polynucleotide sequence. In some embodiments, the polynucleotide is synthesized by sequential couplings of monomer phosphoramidites to the growing terminal of the polynucleotide. The 5'-terminal nucleoside subunit may be attached to any convenient solid support via an optional linking group or 5'-terminal group. Once the first subunit is attached to the solid support, the subunit may be deprotected to produce a free, immobilized 3'-terminal group. Then, subunit couplings to the growing oligonucleotide chain may be achieved. In some instances, the method includes coupling a support bound 3'-terminal group with a 3'-protected-nucleotide-5'-phosphoramidite monomer. In certain embodiments, the 3'-terminal group is a 3'-hydroxyl group. In certain embodiments, the 3'-terminal group is a 3'-amino group.

In some instances, the method of polynucleotide synthesis includes the steps of: (a) deprotecting the protected 3'-amino group of a terminal nucleoside attached to a solid phase support, the deprotecting forming a free 3'-amino group; (b) contacting the free 3'-amino group with a 3'-protected amino-nucleoside-5'-phosphoramidite monomer in the presence of a nucleophilic catalyst to form an internucleoside N3'→P5' phosphoramidite linkage; and (c) oxidizing the linkage to produce a N3'→P5' thiophosphoramidate linkage. In some embodiments, the method includes (d) repeating steps (a) through (c) until the polynucleotide is synthesized.

In some cases, the method includes coupling a support bound 3'-terminal group with a 3'-protected-dinucleotide-5'-phosphoramidite dimer. Polynucleotide synthesis methods of interest include, but are not limited to, those methods of solid phase synthesis including at least one coupling of a dinucleotide dimer as described in PCT Publication No. WO2015/168310 which application claims the benefit of U.S. Provisional Application Ser. No. 61/987,396. The target polynucleotide sequence may be synthesized via a retrosynthetic strategy that includes sequential couplings of both dimer and monomer subunits to the 3'terminal group of the growing oligonucleotide chain. In some embodiments, the polynucleotide is synthesized using a method including at least one coupling of a dinucleotide dimer to the free 3' terminal group of a growing polynucleotide chain.

In some instances, the method of polynucleotide synthesis includes the steps of: (a) deprotecting the protected 3'-amino group of a terminal nucleoside attached to a solid phase support, the deprotecting forming a free 3'-amino group; (b) contacting the free 3'-amino group with a 3'-protected amino-dinucleotide thiophosphoramidate or phosphoramidite-5'-phosphoramidite dimer in the presence of a nucleophilic catalyst to form an internucleoside N3'→P5' phosphoramidite linkage; and (c) oxidizing the linkage a N3'→P5' thiophosphoramidate linkage. In some embodiments, the method includes (d) repeating steps (a) through (c) until the polynucleotide is synthesized, where is step (b) a 3'-protected amino-dinucleotide thiophosphoramidate-5'-phosphoramidite dimer or 3'-protected amino-nucleotide-5'-phosphoramidite monomer may be utilized.

Any convenient protecting group strategies may be utilized in the subject methods to protect the base, phosphoramidite, phosphoramidate, 5',2' and/or 3'groups of the polynucleotide. Protecting groups of interest include, but are not limited to, those protecting groups described by Ohkubo et al., Org. Lett., 2010, 12 (11), pp 2496-2499; and Beaucage and Iyer, Tetrahedron 48: 2223-2311 (1992).

As used herein, the term "phosphate protecting group" refers to a protecting group that may be attached to a phosphorus-containing intersubunit linkage of an oligonucleotide. When present, a phosphate protecting group may prevent (i.e., block) reaction of the phosphorus-containing linkage at the location where the phosphate protecting group is attached. Any convenient phosphorus-containing intersubunit linkages (e.g., P(III) and P(V) linkages) may be protected by the subject phosphate protecting groups, including, but not limited to, phosphoramidite, oxophosphoramidate, thiophosphoramidate, phosphate ester, thiophosphate ester, phosphodiester linkages and the like. The phosphate protecting group may be attached to an available oxygen atom of the phosphorus-containing intersubunit linkage. Any convenient protecting groups may be utilized as a phosphate protecting group. In certain embodiments, a phosphate protecting group is methyl, or β-cyanoethyl.

In some instances, the 3'-terminal group of the growing polynucleotide chain may include a 3'-hydroxyl, a 3'-amino group or a protected version thereof. Any convenient hydroxyl and/or amino protecting groups may be utilized at the 3'-terminal group during polynucleotide synthesis. In some embodiments, the 3'terminal group is a protected 3'-amino group and the method includes deprotecting or removing the protecting group to produce a free 3'amino group. As used herein, the term "free amino group" means an amino group available for reacting with the phosphoramidite group of an incoming monomer or dimer. In some embodiments, a free amino group is a primary amine. After the deprotection (e.g., detritylation) step, the amino group may be in the form of a salt (e.g., the salt of a conjugate base of the acid used for detritylation). This salt may be optionally neutralized with a basic solution such as 2% triethylamine or pyridine in acetonitrile after the detritylation step.

3'-Protection of the incoming subunit phosphoramidites prevents undesirable polymerization of the chain. In some embodiments, the 3'-terminal group is a protected 3'-hydroxyl group and the method includes deprotecting or removing the protecting group to produce a free 3'-hydroxyl group. In some embodiments, the 3'-terminal group is a protected 3'-amino group and the method includes deprotecting or removing the protecting group to produce a free 3'-amino group. The protected 3'-amino or 3'-hydroxyl group may be protected with a trityl protecting group. In certain embodiments, the trityl protecting group is triphenylmethyl (Tr or Trt, $Ph_3C$—). In certain embodiments, the trityl protecting group is 4,4'-dimethoxytrityl (DMT). Deprotection of the 3'-terminal amino or hydroxyl group may be achieved using any convenient methods. Methods of interest include, but are not limited to, those methods described by Beaucage and Iyer, Tetrahedron 48: 2223-2311 (1992). In some cases, deprotection of the protected 3' amino group of a terminal nucleoside includes detritylation to produce a free 3'terminal group, e.g., acid-catalyzed detritylation. In some cases, the dimer or monomer subunit phosphoramidites include a protected 3'-hydroxyl or 3'-amino group that is the same as the 3'-terminal group of the terminal nucleoside attached to the solid support.

Any convenient solid phase supports may be used for the synthesis of polynucleotides according to the subject methods. Solid supports of interest include, but are not limited to, microparticles made of controlled pore glass (CPG), highly cross-linked polystyrene (e.g., NittoPhase HL 400 or GE Primer 350), acrylic copolymers, cellulose, nylon, dextran, latex, polyacrolein, and the like, such as those disclosed in the following exemplary references: Meth. Enzymol., Section A, pages 11-147, vol. 44 (Academic Press, New York, 1976); U.S. Pat. Nos. 4,678,814; 4,413,070; and 4,046,720; and Pon, Chapter 19, in Agrawal, editor, Methods in Molecular Biology, Vol. 20, (Humana Press, Totowa, N.J., 1993). Further supports of interest include polystyrene beads; polystyrene grafted with polyethylene glycol (e.g., TentaGel™, Rapp Polymere, Tubingen Germany); and the like. Selection of the support characteristics, such as material, porosity, size, shape, and the like, and the type of linking moiety employed depends on a variety of factors, such as protection groups employed, length of final product, quantity of final product, and the like. Exemplary linking moieties are disclosed in Pon et al., Biotechniques, 6:768-775 (1988); Webb, U.S. Pat. No. 4,659,774; Barany et al., International patent application PCT/US91/06103; Brown et al., J. Chem. Soc. Commun., 1989: 891-893; Damha et al., Nucleic Acids Research, 18: 3813-3821 (1990); Beattie et al., Clinical Chemistry, 39: 719-722 (1993); Maskos and Southern, Nucleic Acids Research, 20: 1679-1684 (1992); and the like.

In some embodiments, the solid supports that find use in the subject methods include CPG and polystyrene grafted with polyethylene glycol and possessing a terminal amino group (e.g., TentaGel-$NH_2$™, Rapp Polymere, Tubingen Germany). The aminopropyl group may be used as a spacer between CPG and the nucleoside linkage. In some cases, the linkage to the 5'-hydroxyl of the first nucleoside is a succinyl group which provides a base-labile ester linkage that may be cleaved after synthesis with aqueous ammonia.

Following deprotection, the support-bound nucleoside is capable of reacting with a dimer or monomer subunit phosphoramidite to form an internucleoside linkage. It is understood that the support-bound nucleoside may refer to a single residue attached to a solid support or may refer to the terminal residue of an oligonucleotide chain that is attached to the support. Any convenient coupling chemistry, coupling reagents and methods may be utilized in the subject methods. Any convenient selections concerning coupling conditions, protecting groups, solid phase supports, linking groups, deprotection reagents, reagents to cleave products from solid phase supports, purification of product, and the like, may be made in the context of the subject methods according to the guidance of, e.g. Gait, editor, Oligonucleotide Synthesis: A Practical Approach (IRL Press, Oxford, 1984); Amarnath and Broom, Chemical Reviews, Vol. 77, pgs. 183-217 (1977); Pon et al., Biotechniques, Vol. 6, pgs. 768-775 (1988); Ohtsuka et al., Nucleic Acids Research, Vol. 10, pgs. 6553-6570 (1982); Eckstein, editor Oligonucleotides. and Analogues: A Practical Approach (IRL Press, Oxford, 1991), Greene and Wuts "Protective Groups in Organic Synthesis", Third edition, Wiley, New York 1999, Narang, editor, Synthesis and Applications of DNA and RNA (Academic Press, New York, 1987), Beaucage and Iyer, Tetrahedron 48: 2223-2311 (1992), and like references.

In some instances, after coupling, unreacted 3'-amino groups of a support-bound growing chain of the polynucleotide may be optionally capped with a convenient capping agent before the next deprotection step (e.g., detritylation step) to render them inert to subsequent coupling steps. This capping step may improve the HPLC profile of the preparation to make purification more facile, and may also improve the overall yield of product. Capping reagents useful in the subject methods include electrophilic reagents such as acetic anhydride and isobutyric anhydride, acid chlorides such as adamantyl carbonyl chloride, pivaoyl chloride, and the like, isothiocyanates, chloroformates, etc. Also useful are phosphoramidites in conjunction with an activator and followed by oxidation, and H-phosphonate salts such as triethylammonium isopropyl-H-phosphonate used in conjunction with an acid chloride such as pivaoyl chloride or adamantyl carbonyl chloride.

In some embodiments, the method includes oxidizing an internucleoside N3'→P5' phosphoramidite linkage. As used herein, the terms "oxidize," "oxidation," "oxidizing", and the like, in reference to a phosphorus-containing internucleosidic linkage means a process or treatment for converting the phosphorus atom of the linkage from a phosphorus (III) form to a phosphorus (V) form. Oxidation of the internucleotide linkages may be performed at any convenient point in the synthesis using any convenient methods. In some embodiments, oxidation is performed in a stepwise manner, e.g., during every coupling cycle. In other embodiments, oxidation of multiple internucleotide linkages is performed at the end of the synthesis. In some instances, oxidizing a N3'→P5' phosphoramidite linkage (e.g., using an iodine/water based oxidizing agent) produces an oxophosphoramidate linkage. In other instances, oxidizing a N3'→P5' phosphoramidite linkage includes sulfurization to produce a N3'→P5' thiophosphoramidate linkage. Sulfurization may be performed using any convenient methods. Sulfurization methods of interest include those described by Gryazonov et al. in WO2001018015 and U.S. Pat. No. 6,114,519. Sulfurizing agents of interest include, but are not limited to, elemental sulfur, thiuram disulfides such as tetraethyl thiuram disulfide, acyl disulfides such as phenacyldisulfide, phenyl acetyl disulfide, phosphinothioyl disulfides such as S-Tetra™, and 1,1-dioxo-3H-1,2-benzodithiol-3-one. In some embodiments, sulfurization may be performed using phenyl acetyl disulfide in 2,6-lutidine. In certain embodiments, sulfurization may be performed using Beaucage reagent, using methods as described by Iyer et al., J. Organic Chemistry 55:4693-4699, 1990.

Cleavage of the polynucleotide from the solid phase synthesis support may be achieved using any convenient methods and reagents, which may be selected depending on a variety of factors, such as the nature of the support, linker chemistry and the protecting group strategy utilized during synthesis. The selections made in the synthesis and cleavage of a target polynucleotide may determine the identities of the non-target synthesis products and agent present in the first polynucleotide composition.

In some embodiments, prior to cleavage, the phosphorus protecting groups of the polynucleotide are removed to avoid the formation of any potential undesirable adducts of the cleaved protecting group (e.g., the β-cyanoethyl protecting group) with the polynucleotide. Methods of interest that may be adapted for use in deprotecting and cleaving polynucleotides include those described in U.S. Pat. No. 7,199,236. In some embodiments, the polynucleotide is cleaved from the support using an ammonia solution to remove any base protecting groups (e.g., exocyclic amino protecting groups) and any remaining phosphorus protecting groups. Any convenient conditions may be utilized in the polynucleotide cleavage reaction. In some cases, the cleavage is performed at a temperature in the range of 40-60° C. In some instances, the cleavage is performed over an extended period of time, such as a time in the range of 12-24 hours. Post cleavage of the polynucleotide, the support may then be removed by filtration and rinsed. The combined filtrate and rinse solutions, which now contain the crude synthetic preparation of polynucleotide, may be utilized in the subject methods of preparation, before being carried forward to further purification steps. In some cases, purification of a polynucleotide solution includes preparative Reversed Phase-High Performance Liquid Chromatography (RP-HPLC) RP HPLC, e.g., using Kromasil C18 at 45-55° C. In some instances, the polynucleotide compositions of the subject methods may undergo any number of convenient desalting and concentration steps, e.g., by using a Tangential Flow Filtration (TFF) apparatus equipped with polyethersulfone membranes with a pore diameter cut-off size of 1,000 Da.

Polynucleotide Compositions

Aspects of the present disclosure include polynucleotide salt compositions including multivalent cation counterions. In some embodiments, the composition includes: a salt of a polynucleotide including at least one multivalent cation counterion, where the polynucleotide has a sequence of 7 or more nucleoside subunits and at least two of the nucleoside subunits are joined by a N3'→P5' thiophosphoramidate inter-subunit linkage. In certain embodiments, the polynucleotide has a sequence of 7 or more nucleoside subunits complementary to the RNA component of human telomerase.

Multivalent Cation Counterions

Any convenient multivalent cations may find use as a counterion in the subject polynucleotide salts. As such, a multivalent cation may form an ion pair with an anionic site on a polynucleotide backbone in the subject polynucleotide compositions. Polynucleotides may include nucleoside subunits linked by phosphorus-containing intersubunit linkages (e.g., P(V) linkages) such as phosphoramidate, thiophosphoramidate, phosphate ester, phosphodiester linkages and the like. It is understood that the intersubunit linkages of the polynucleotide may be negatively charged (e.g., in an aqueous solution) and ion paired with a cationic counterion. Such intersubunit linkages may be referred to as anionic groups of the polynucleotide backbone.

As used herein, the term multivalent cation refers to a cation capable of forming multiple ion pairs, e.g., a multiply charged cation, such as a double charged or a triply charged cation. Any convenient multivalent cations may find use in the subject polynucleotide salt compositions. In some embodiments, a multivalent cation ion pairs to two or more adjacent anionic groups of the polynucleotide backbone. In some embodiments, a multivalent cation ion pairs to one anionic group of the polynucleotide backbone. In some embodiments, the multivalent cation counterion is divalent. Divalent cation counterions of interest include, but are not limited to, magnesium, zinc and calcium. In some embodiments, the multivalent cation counterion is trivalent. Trivalent cation counterions of interest include, but are not limited to, aluminium. In certain embodiments of the composition, the at least one multivalent cation counterion is selected from the group consisting of magnesium, zinc, aluminium and calcium. In certain embodiments of the composition, the at least one multivalent cation counterion is magnesium. In certain embodiments of the composition, the at least one multivalent cation counterion is zinc. In certain embodiments of the composition, the at least one multivalent cation counterion is aluminium. In certain embodiments of the composition, the at least one multivalent cation counterion is calcium.

It is understood that the number of cation counterions that are present in a polynucleotide salt is dependent on a variety of factors, such as the length of the polyanionic backbone, the valency of the cations in the salts, the pH of the solution, aggregation of polynucleotides in the composition, etc. The subject compositions may include at least one multivalent cation counterion to the polyanionic polynucleotide backbone in the subject polynucleotide compositions, such as 2 or more, 3 or more, 4 or more, 5 or more, 6 or more, 7 or more, 8 or more, 9 or more, 10 or more, 15 or more, 20 or more, 30 or more, 40 or more, 50 or more, 100 or more, or even more multivalent cation counterions. In certain embodiments, a polynucleotide having n nucleoside subunits may include between 1 and $(n-1)/2$ (if n is an odd integer) divalent cation counterion(s) or between 1 and $(n-2)/2$ (if n is an even integer) divalent cation counterion(s). In some instances, a polynucleotide salt that includes at least one multivalent cation, may further include a variety of other cation counterions, which may be monovalent, divalent or trivalent. In certain instances, n is in the range of 7 to 50, such as 7 to 40, 10 to 40, 10 to 30, 10 to 25, 10 to 20, or in the range of 12 to 15 nucleoside subunits.

In some embodiments of the composition, the polynucleotide salt may include 3 mol % or more of the multivalent cation counterion relative to a polyanionic backbone of the polynucleotide (i.e., relative to a theoretical maximum inclusion of cation counterions along the polyanionic backbone), such as 4 mol % or more, 5 mol % or more, 6 mol % or more, 7 mol % or more, 8 mol % or more, 9 mol % or more, 10 mol % or more, 11 mol % or more, 12 mol % or more, 13 mol % or more, 14 mol % or more, 15 mol % or more, 16 mol % or more, 17 mol % or more, 18 mol % or more, 19 mol % or more, 20 mol % or more, 25 mol % or more, 30 mol % or more, 35 mol % or more, 40 mol % or more, 45 mol % or more, 50 mol % or more, 55 mol % or more, 60 mol % or more, or even more, of the multivalent cation counterion relative to a polyanionic backbone of the polynucleotide. In some embodiments of the subject compositions, the polynucleotide may include 10 mol % or more of the multivalent cation counterion relative to a polyanionic backbone of the polynucleotide. For example, a polynucleotide salt that includes a polyanionic backbone of 10 internucleoside subunit linkages and includes one divalent cation counterion ion pairing to two of the linkages, is described as including 20 mol % of the divalent cation counterion. If the one divalent cation counterion ion pairs to only one of the linkages instead of two, the polynucleotide salt is described as including 10 mol % of the divalent cation counterion. As such, the mol % value refers to a level of occupation of the polyanionic polynucleotide backbone by the multivalent cation counterions that are present in the polynucleotide salt. For example, one $Mg^{2+}$ cation in a 13-mer polynucleotide salt having 12 internucleoside subunit linkages gives 16.7 mol % occupation of the backbone. It is understood that in some embodiments, the polynucleotide salt may include additional ion pairing sites at the terminals of the polynucleotide (e.g., a 5'-thiophosphate group), and if present, such sites should be included in the mol % value of the compound.

In some embodiments of the composition, the polynucleotide salt includes 90 mol % or less of the multivalent cation counterion relative to a polyanionic backbone of the polynucleotide, such as 70 mol % or less, 65 mol % or less, 60 mol % or less, 50 mol % or less, or even less of the multivalent cation counterion.

In certain embodiments of the composition, the polynucleotide salt includes 3 to 90 mol % of the multivalent cation counterion relative to a polyanionic backbone of the polynucleotide, such as 3 to 65 mol % (e.g., 6 to 50 mol %, 10 to 50 mol % or 10 to 40 mol %), 3 to 50 mol %, 3 to 40 mol %, 3 to 30 mol %, 3 to 20 mol % or 3 to 15 mol % of the multivalent cation counterion relative to a polyanionic backbone of the polynucleotide.

In certain instances of the composition, the polynucleotide salt includes 3 to 60 mol % of a divalent cation counterion relative to a polyanionic backbone of the polynucleotide, such as 3 to 50 mol % (e.g., 5 to 50 mol %), 3 to 40 mol %, 3 to 30 mol %, 3 to 20 mol %, 3 to 15 mol %, such as 3-12 mol % of a divalent cation counterion, In certain instances of the composition, the polynucleotide salt includes 3 to 60 mol % of a magnesium cation counterion relative to a polyanionic backbone of the polynucleotide, such as magnesium, 5-50 mol %, 5-40 mol %, 10-40 mol % or 20-40 mol % of a magnesium cation counterion.

In certain instances of the composition, the polynucleotide salt includes 10 to 70 mol % of a trivalent cation counterion relative to a polyanionic backbone of the polynucleotide, such as 10 to 60 mol %, 20 to 60 mol %, 20 to 50 mol % or 30 to 50 mol % of a trivalent cation counterion. In some embodiments of the composition, the polynucleotide salt includes 0.5% or more by weight of the multivalent cation counterion (e.g., magnesium), such as 0.6% or more, 0.7% or more, 0.8% or more, 0.9% or more, 1.1% or more, 1.2% or more, 1.3% or more, 1.4% or more, 1.5% or more, 1.6% or more, 1.7% or more, 1.8% or more, 1.9% or more, 2.0% or more, 2.1% or more, 2.2% or more, 2.3% or more 2.4% or more, 2.5% or more, 2.6% or more, 2.7% or more, 2.8 or more, 2.9% or more, 3.0% or more by weight of the multivalent cation counterion.

The polynucleotide salt is a mixed salt that includes a mixture of multivalent and monovalent cation counterions. In certain embodiments of the composition, the polynucleotide salt includes a ratio of multivalent cation counterion to monovalent cation counterion of at least 0.05 or more by molarity, such as 0.10 or more, 0.15 or more, 0.20 or more, 0.25 or more, 0.30 or more, 0.35 or more, 0.40 or more, 0.45 or more, 0.50 or more, 0.55 or more, 0.60 or more, 0.65 or more, 0.70 or more by molarity, or even more of multivalent cation counterion to monovalent cation counterion.

In some instances, the polynucleotide salt includes a ratio of multivalent to monovalent cation counterion of 1:12 by molarity. In some instances, the polynucleotide salt includes a ratio of multivalent to monovalent cation counterion of 1:11 by molarity. In some instances, the polynucleotide salt includes a ratio of multivalent to monovalent cation counterion of 1:10 by molarity. In some instances, the polynucleotide salt includes a ratio of multivalent to monovalent cation counterion of 1:9 by molarity. In some instances, the polynucleotide salt includes a ratio of multivalent to monovalent cation counterion of 1:8 by molarity. In some instances, the polynucleotide salt includes a ratio of multivalent to monovalent cation counterion of 1:7 by molarity. In some instances, the polynucleotide salt includes a ratio of multivalent to monovalent cation counterion of 1:6 by molarity. In some instances, the polynucleotide salt includes a ratio of multivalent to monovalent cation counterion of 1:5 by molarity. In some instances, the polynucleotide salt includes a ratio of multivalent to monovalent cation counterion of 1:4 by molarity. In some instances, the polynucleotide salt includes a ratio of multivalent to monovalent cation counterion of 2:9 by molarity. In some instances, the polynucleotide salt includes a ratio of multivalent to monovalent cation counterion of 3:7 by molarity. In some instances, the polynucleotide salt includes a ratio of multivalent to monovalent cation counterion of 4:5 by molarity. In some instances, the polynucleotide salt includes a ratio of multivalent to monovalent cation counterion of 5:3 by molarity.

In certain instances of the mixed polynucleotide salt, the multivalent cation counterion is magnesium and the monovalent cation counterion is sodium. In certain instances of the mixed polynucleotide salt, the multivalent cation counterion is magnesium and the monovalent cation counterion is ammonium. In certain instances of the mixed polynucleotide salt, the multivalent cation counterion is magnesium and the monovalent cation counterion is triethylammonium. In certain instances of the mixed polynucleotide salt, the multivalent cation counterion is aluminium. In certain instances of the mixed polynucleotide salt, the multivalent cation counterion is zinc. In certain instances of the mixed polynucleotide salt, the multivalent cation counterion is calcium. In certain instances of the mixed polynucleotide salt, the monovalent cation counterion is sodium. In certain instances of the mixed polynucleotide salt, the monovalent cation counterion is ammonium. In certain instances of the mixed polynucleotide salt, the monovalent cation counterion is triethylammonium. In certain embodiments, the polynucleotide salt includes one multivalent cation counterion. In certain embodiments, the polynucleotide salt includes 2 multivalent cation counterions. In certain embodiments, the polynucleotide salt includes 3 multivalent cation counterions. In certain embodiments, the polynucleotide salt includes 4 multivalent cation counterions. In certain embodiments, the polynucleotide salt includes 5 multivalent cation counterions. In certain embodiments, the polynucleotide salt includes 6 multivalent cation counterions. In certain embodiments, the polynucleotide salt includes 7 multivalent cation counterions. In certain embodiments, the polynucleotide salt includes 8 multivalent cation counterions. In certain embodiments, the polynucleotide salt includes 9 multivalent cation counterions. In certain embodiments, the polynucleotide salt includes 10 multivalent cation counterions.

In addition to a target polynucleotide, a variety of non-target polynucleotide synthesis products may be produced during polynucleotide synthesis. Minor products that may be present in polynucleotide preparations include, but are not limited to, deletion products (e.g., products lacking one or more nucleoside residues), products that include one or more protecting groups, terminated products (e.g., products that include a capped polynucleotide chain), products that lack one or more nucleobases, products that include partially oxidized phosphoramidite linkages and products that include partially sulfurized linkages.

The subject methods provide for compositions that include an improved purity of target polynucleotide in the composition. In some embodiments, the composition includes 20% or more by weight of the target polynucleotide, such as 25% or more, 30% or more, 35% or more, 40% or more, 45% or more, 50% or more, 60% or more, 70% or more, 80% or more, 90% or more, or even 95% or more by weight of the target polynucleotide. In certain embodiments, the composition includes 50% or more by weight of the target polynucleotide. In certain embodiments, the composition includes 55% or more by weight of the target polynucleotide. In certain embodiments, the composition includes 60% or more by weight of the target polynucleotide. In certain embodiments, the composition includes 65% or more by weight of the target polynucleotide. In certain embodiments, the composition includes 70% or more by weight of the target polynucleotide. In certain embodiments, the composition includes 75% or more by weight of the target polynucleotide. In certain embodiments, the composition includes 80% or more by weight of the target polynucleotide. In certain embodiments, the composition includes 85% or more by weight of the target polynucleotide. In certain embodiments, the composition includes 90% or more by weight of the target polynucleotide. In certain embodiments, the composition includes 95% or more by weight of the target polynucleotide.

The subject methods provide for compositions including a reduced amount of non-target synthesis products and agents. By reduced amount is meant that the amount by weight of the non-target synthesis products and agents in the composition is reduced relative to a control method. In some embodiments, the subject compositions include non-target synthesis products and agents in an amount of 50% or less of the total non-target polynucleotides in the composition, such as 40% or less, 30% or less, 25% or less, 20% or less, 15% or less, 10% or less or even 5% or less of the non-target synthesis products and agents.

Any of a wide variety of polynucleotide compositions can be prepared using the methods described herein. A variety of classes and types of polynucleotides are of interest for preparation using the subject methods (e.g., as described herein). Polynucleotides suitable for preparation according to the subject methods include, but are not limited to, anti-sense polynucleotides, RNA polynucleotides, siRNA polynucleotides, RNAi polynucleotides, DNA aptamers, micro RNA and the like.

In some embodiments, the polynucleotide is described by Formula (I):

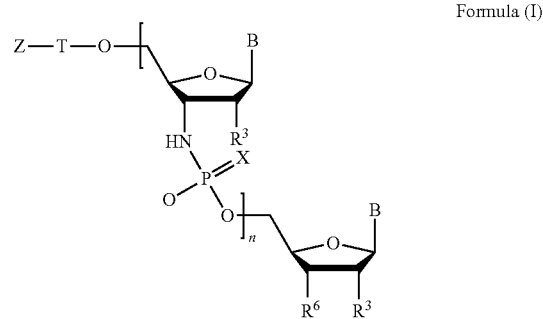

Formula (I)

wherein:
each B is independently a purine, a protected purine, a pyrimidine or a protected pyrimidine, or an analog thereof;
each X is independently oxygen or sulfur;
each $R^3$ is independently hydrogen, fluoro, hydroxyl, an alkoxy, a substituted alkoxy or a protected hydroxyl;
$R^6$ is amino, hydroxyl, a protected amino, a protected hydroxy, —O-T-Z or —NH-T-Z;
each T is independently an optional linker;
each Z is independently H, a lipid, a carrier, an oligonucleotide, a polymer, a polypeptide, a detectable label, or a tag; and n is an integer of 1 to 1000. It is understood that the oligonucleotides of Formula (I), may exist in a salt form. As such, the internucleoside linkages of Formula (I) may be in a salt form that includes any convenient counterion. Such forms are intended to be included within the scope of the present disclosure. It is understood that other tautomeric arrangements of the internucleoside linkages of the polynucleotide described in Formula (I) may be possible. Such forms are intended to be included within the scope of the present disclosure.

In some embodiments of Formula (I), each $R^3$ is hydrogen. In some embodiments of Formula (I), each $R^3$ is fluoro. In some embodiments of Formula (I), each $R^3$ is hydroxyl. In some embodiments of Formula (I), $R^6$ is amino. In certain embodiments of Formula (I), $R^6$ is hydroxyl. In some embodiments of Formula (I), Z is H. In some embodiments of Formula (I), Z is a lipid (e.g., as described herein). In certain cases, the lipid is a fatty acid (e.g., as described herein). In some embodiments of Formula (I), Z is a carrier. In some embodiments of Formula (I), Z is an oligonucleotide. In some embodiments of Formula (I), Z is a polymer. In certain cases, the polymer is a PEG. In some embodiments of Formula (I), Z is a polypeptide. In some embodiments of Formula (I), Z is a detectable label. In some embodiments of Formula (I), Z is a tag. In some embodiments of Formula (I), T is absent. In some embodiments, each B is independently selected from A, C, G, T and U.

In certain embodiments of Formula (I), n is an integer of between 7 and 500, such as between 7 and 100, between 7 and 75, between 7 and 50, between 7 and 40, between 7 and 30, between 7 and 20, between 7 and 15, between 10 and 15, or between 13 and 15. In certain embodiments, n is an integer of between 7 and 100, such as between 7 and 50, between 10 and 50, between 10 and 40, between 10 and 30, between 10 and 25, between 10 and 20, between 12 and 18, or between 12 and 16. In certain embodiments, n is 7, 8, 9, 10, 11, 12, 13, 14, 15, 16, 17, 18, 19, 20, 21, 22, 23, 24 or 25.

Polynucleotides Complementary to RNA Component of Telomerase

Aspects of the disclosure include compounds and compositions including polynucleotides complementary to the RNA component of human telomerase, and methods for preparing the same. The compounds may inhibit telomerase activity in cells with a high potency and have cellular uptake characteristics.

In certain instances, the polynucleotide includes a sequence of 7 or more nucleoside subunits complementary to the RNA component of human telomerase, such as 8 or more, 9 or more, 10 or more, 11 or more, 12 or more, 13 or more, 14 or more, 15 or more, 20 or more, 30 or more, 50 or more nucleoside subunits complementary to the RNA component of human telomerase.

In some embodiments, the polynucleotide includes between 3 and 50 contiguous nucleoside subunits complementary to the RNA component of human telomerase, such as between 5 and 40, between 7 and 40, 10 and 40, between 10 and 30, between 10 and 25, between 10 and 20, or between 12 and 15 nucleoside subunits. In certain embodiments, the polynucleotide includes a sequence of 7 or more contiguous nucleoside subunits complementary to the RNA component of human telomerase, such as 10 or more, 11 or more, 12 or more, 13 or more, 14 or more, 15 or more, 20 or more, 30 or more, 50 ced contiguous nucleoside subunits complementary to the RNA component of human telomerase.

In some embodiments, the polynucleotide is a compound described by the formula:

O-(x-L)$_n$ where O represents the polynucleotide including a sequence of nucleoside subunits complementary to the RNA component of human telomerase, x is an optional linker group, L represents a lipid moiety and n is an integer from 1-5. In some instances, n is 5. In some instances, n is 4. In some instances, n is 3. In some instances, n is 2. In some instances, n is 1. Design of the compounds therefore requires the selection of two entities, O and L, and the determination of the structural linkage(s) between these entities, which may involve the optional linker group x.

In some embodiments, the polynucleotide compound may be described by the formula:

O-(x-L)$_n$ where O represents the polynucleotide including a sequence of nucleoside subunits complementary to the RNA component of human telomerase, x is an optional linker group, L represents the lipid moiety and n is 1, such as a polynucleotide of Formula (I), or a salt thereof, wherein in Formula (I), Z is the lipid moiety, T is the optional linker (e.g., as described herein) and the B groups correspond to the sequence of nucleoside subunits complementary to the RNA component of human telomerase.

The polynucleotide component O may be regarded as the "effector" component of the compound in that it is this component that effects inhibition of the telomerase enzyme by binding to the RNA component of telomerase. Thus, the sequence of O is selected such that it includes a region that is complementary to the sequence of the telomerase RNA, which is shown in SEQ ID NO:1. The region that is complementary to the telomerase RNA component may in theory be targeted to any portion of the telomerase RNA, but particular regions of the telomerase RNA are preferred targets for inhibitory polynucleotides. One preferred target region is the region spanning nucleotides 30-67 of SEQ ID NO:1, which includes the "template region," an 11 nucleotide region of sequence 5'-CUAACCCUAAC-3' (SEQ ID NO: 21) that spans nucleotide 46-56 of SEQ ID NO: 1. The template region functions to specify the sequence of the telomeric repeats that telomerase adds to the chromosome ends and is essential to the activity of the telomerase enzyme (see Chen et al., Cell 100:503-514, 2000; Kim et al., Proc. Natl. Acad. Sci., USA 98(14):7982-7987, 2001). Compounds of interest that contain a polynucleotide moiety including a sequence complementary to all or part of the template region are thus of interest. Another target region of interest is the region spanning nucleotides 137-179 of hTR (see Pruzan et al., Nucl. Acids Research, 30:559-588, 2002). Within this region, the sequence spanning 141-153 is a preferred target. PCT publication WO 98/28442 describes the use of polynucleotides of at least 7 nucleotides in length to inhibit telomerase, where the polynucleotides are designed to be complementary to accessible portions of the hTR sequence outside of the template region, including nucleotides 137-196, 290-319, and 350-380 of hTR.

The region of O that is targeted to the hTR sequence is in some cases exactly complementary to the corresponding hTR sequence. While mismatches may be tolerated in certain instances, they are expected to decrease the specificity and activity of the resultant polynucleotide conjugate. In some embodiments, the base sequence of the polynucleotide O is thus selected to include a sequence of at least 5 nucleotides exactly complementary to the telomerase RNA, and enhanced telomerase inhibition may be obtained if increasing lengths of complementary sequence are employed, such as at least 6, at least 7, at least 8, at least 10, at least 12, at least 13 or at least 15 nucleotides exactly complementary to the telomerase RNA. In other embodiments, the sequence of the polynucleotide includes a sequence of from at least 7 to 20, from at least 8 to 20, from at least 10 to 20 or from at least 10 to 15 nucleotides exactly complementary to the telomerase RNA sequence. Optimal telomerase inhibitory activity may be obtained when the full length of the polynucleotide O is selected to be complementary to the telomerase RNA. However, it is not necessary that the full length of the polynucleotide component be exactly complementary to the target sequence, and the polynucleotide sequence may include regions that are not complementary to the target sequence. Such regions may be added, for example, to confer other properties on the compound, such as sequences that facilitate purification. If the polynucleotide component O is to include regions that are not complementary to the target sequence, such regions may be positioned at one or both of the 5' or 3' termini. In instances where the region of exact complementarity is targeted to the template region, effective telomerase inhibition may be achieved with a short (5-8 nucleotide) region of exact complementarity to which a telomerase-like (G-rich) sequence is joined at the 5' end.

Exemplary sequences that are complementary to the human telomerase RNA and which may be included as part of the polynucleotide component O, or which may be used as the entire polynucleotide component O include the following:

hTR complementary sequences (regions of Polynucleotide sequence SEQ ID NO:1 of U.S. Publication 2012329858);

```
                                              (SEQ ID NO: 1)
GGGUUGCGGA GGGUGGGCCU GGGAGGGGUG GUGGCCAUUU

UUUGUCUAAC CCUAACUGAG AAGGGCGUAG GCGCCGUGCU

UUUGCUCCCC GCGCGCUGUU UUUCUCGCUG ACUUUCAGCG

GGCGGAAAAG CCUCGGCCUG CCGCCUUCCA CCGUUCAUUC

UAGAGCAAAC AAAAAAUGUC AGCUGCUGGC CCGUUCGCCC

CUCCCGGGGA CCUGCGGCGG GUCGCCUGCC CAGCCCCCGA

ACCCCGCCUG GAGGCCGCGG UCGGCCCGGG GCUUCUCCGG

AGGCACCCAC UGCCACCGCG AAGAGUUGGG CUCUGUCAGC

CGCGGGUCUC UCGGGGGCGA GGGCGAGGUU CAGGCCUUUC

AGGCCGCAGG AAGAGGAACG GAGCGAGUCC CCGCGCGCGG

CGCGAUUCCC UGAGCUGUGG GACGUGCACC CAGGACUCGG

CUCACACAUG C
                                              (SEQ ID NO: 2)
GCTCTAGAATGAACGGTGGAAGGCGGCAGG 137-166

(SEQ ID NO: 6)
GTGGAAGGCGGCAGG 137-151

(SEQ ID NO: 7)
GGAAGGCGGCAGG 137-149

(SEQ ID NO: 8)
GTGGAAGGCGGCA 139-151

(SEQ ID NO: 9)
GTGGAAGGCGG 141-151

(SEQ ID NO: 10)
CGGTGGAAGGCGG 141-153

(SEQ ID NO: 11)
ACGGTGGAAGGCG 142-154

(SEQ ID NO: 12)
AACGGTGGAAGGCGGC 143-155
```

```
-continued
                                              (SEQ ID NO: 13)
ATGAACGGTGGAAGGCGG 144-158

(SEQ ID NO: 14)
ACATTTTTTGTTTGCTCTAG 160-179

(SEQ ID NO: 3)
TAGGGTTAGACAA 42-54

(SEQ ID NO: 4)
GTTAGGGTTAG 46-56

(SEQ ID NO: 15)
GTTAGGGTTAGAC 44-56

(SEQ ID NO: 16)
GTTAGGGTTAGACAA 42-56

(SEQ ID NO: 19)
GGGTTAGAC 44-52

(SEQ ID NO: 20)
CAGTTAGGG 50-58

(SEQ ID NO: 17)
CCCTTCTCAGTT 54-65

(SEQ ID NO: 18)
CGCCCTTCTCAG 56-67
```

In some embodiments, the polynucleotide includes a sequence selected from the group consisting of: GTTAGGGTTAG (SEQ ID NO:4); TAGGGTTAGACAA (SEQ ID NO:3); and CAGTTAGGGTTAG (SEQ ID NO:5).

The choice of the type of inter-nucleoside linkages used in the synthesis of the O component may be made from any of the available polynucleotide chemistries, including but not limited to, phosphodiester, phosphotriester, methylphosphonate, P3'→N5' phosphoramidate, N3'→P5' phosphoramidate, N3'→P5' thiophosphoramidate, and phosphorothioate linkages. In some embodiments, the polynucleotide component O has at least one N3 thiophosphoramidate linkage. In certain embodiments, the nucleoside subunits complementary to the RNA component of human telomerase are all joined by N3'→P5' thiophosphoramidate inter-subunit linkages. In certain cases, the N3'→P5' thiophosphoramidate inter-subunit linkage has the following structure:

3'-NH—P(S)(OR)—O—5' where R is hydrogen, or a salt thereof. It is understood that for any of the polynucleotide components O described herein that include such an inter-subunit linkage, such polynucleotide components O may also include any convenient salt forms of the linkage. As such, the inter-subunit linkage may be in a salt form that includes any convenient counterion.

In some embodiments, at least two of the nucleoside subunits are joined by a N3'→P5' thiophosphoramidate inter-subunit linkage, and the other inter-subunit linkages each independently are selected from N3'→P5' oxo-phosphoramidate and N3'→P5' thiophosphoramidate inter-subunit linkages. In some embodiments, the nucleoside subunits are joined by inter-subunit linkages each independently selected from N3'→P5' oxo-phosphoramidate and N3'→P5' thiophosphoramidate inter-subunit linkages. In some embodiments, the nucleoside subunits are joined by inter-subunit linkages each independently selected from N3'→P5' oxo-phosphoramidate and N3'→P5' thiophosphoramidate inter-subunit linkages; provided that at least two of the nucleoside subunits are joined by a N3'→P5' thiophosphoramidate inter-subunit linkage. In some embodiments, the nucleoside subunits are joined by are all joined by N3'→P5' thiophosphoramidate inter-subunit linkages.

In some embodiments, the polynucleotide component O has the sequence TAGGGTTAGACAA (SEQ ID NO:3), and the nucleoside subunits are joined by inter-subunit linkages comprising at least one N3'→P5' thiophosphoramidate linkage. In some embodiments, the polynucleotide component O has the sequence TAGGGTTAGACAA (SEQ ID NO:3), and the nucleoside subunits are joined by inter-subunit linkages comprising at least two N3'→P5' thiophosphoramidate linkages. In some embodiments, the polynucleotide component O has the sequence TAGGGTTAGACAA (SEQ ID NO:3), and the nucleoside subunits are joined by inter-subunit linkages comprising at least three N3'→P5' thiophosphoramidate linkages. In some embodiments, the polynucleotide component O has the sequence TAGGGTTAGACAA (SEQ ID NO:3), and the nucleoside subunits are joined by inter-subunit linkages comprising at least four N3'→P5' thiophosphoramidate linkages. In some embodiments, the polynucleotide component O has the sequence TAGGGTTAGACAA (SEQ ID NO:3), and the nucleoside subunits are joined by inter-subunit linkages comprising at least five N3'→P5' thiophosphoramidate linkages. In some embodiments, the polynucleotide component O has the sequence TAGGGTTAGACAA (SEQ ID NO:3), and the nucleoside subunits are joined by inter-subunit linkages comprising at least six N3'→P5' thiophosphoramidate linkages. In some embodiments, the polynucleotide component O has the sequence TAGGGTTAGACAA (SEQ ID NO:3), and the nucleoside subunits are joined by inter-subunit linkages comprising at least seven N3'→P5' thiophosphoramidate linkages. In some embodiments, the polynucleotide component O has the sequence TAGGGTTAGACAA (SEQ ID NO:3), and the nucleoside subunits are joined by inter-subunit linkages comprising at least eight N3'→P5' thiophosphoramidate linkages. In some embodiments, the polynucleotide component O has the sequence TAGGGTTAGACAA (SEQ ID NO:3), and the nucleoside subunits are joined by inter-subunit linkages comprising at least nine N3'→P5' thiophosphoramidate linkages. In some embodiments, the polynucleotide component O has the sequence TAGGGTTAGACAA (SEQ ID NO:3), and the nucleoside subunits are joined by inter-subunit linkages comprising at least ten N3'→P5' thiophosphoramidate linkages. In some embodiments, the polynucleotide component O has the sequence TAGGGTTAGACAA (SEQ ID NO:3), and the nucleoside subunits are joined by inter-subunit linkages comprising at least eleven N3'→P5' thiophosphoramidate linkages. In some embodiments, the polynucleotide component O has the sequence TAGGGTTAGACAA (SEQ ID NO:3), and the nucleoside subunits are joined by inter-subunit linkages each independently selected from N3'→P5' oxo-phosphoramidate and N3'→P5' thiophosphoramidate inter-subunit linkages. In some embodiments, the polynucleotide component O has the sequence TAGGGTTAGACAA (SEQ ID NO:3), and the nucleoside subunits are joined by inter-subunit linkages each independently selected from N3'→P5' oxo-phosphoramidate and N3'→P5' thiophosphoramidate inter-subunit linkages; provided that at least two of the nucleoside subunits are joined by a N3'→P5' thiophosphoramidate inter-subunit linkage. In some embodiments, the polynucleotide component O has the sequence TAGGGTTAGACAA (SEQ ID NO:3), and the nucleoside subunits are all joined by N3'→P5' thiophosphoramidate inter-subunit linkages.

In all embodiments hereinbefore and hereinafter, N3'→P5' thiophosphoramidate inter-subunit linkages in particular are —NH—P(=O)(SH)—O— or a tautomer thereof, or a salt thereof; and N3'→P5' oxo-phosphoramidate inter-subunit linkages in particular are —NH—P(=O)(OH)—O— or a tautomer thereof, or a salt thereof. More in particular, in all embodiments hereinbefore and hereinafter, N3'→P5' thiophosphoramidate inter-subunit linkages in particular are —NH—P(=O)(SH)—O— or a tautomer thereof, or a sodium salt thereof; and N3'→P5' oxo-phosphoramidate inter-subunit linkages in particular are —NH—P(=O)(OH)—O— or a tautomer thereof, or a sodium salt thereof.

In one of the embodiments, the invention relates to any one of the specific structures described herein wherein optionally one or more, in particular one, N3'→P5' thiophosphoramidate inter-subunit linkages are replaced by N3'→P5' oxo-phosphoramidate inter-subunit linkages. In one of the embodiments, the invention relates to any one of the specific structures described herein wherein one or more, in particular one, N3'→P5' thiophosphoramidate inter-subunit linkages are replaced by N3'→P5' oxo-phosphoramidate inter-subunit linkages.

In some cases, the subject compounds are more effective in producing telomerase inhibition in cells than corresponding polynucleotides that are not conjugated to lipid components. The lipid component L is believed to function to enhance cellular uptake of the compound, particularly in facilitating passage through the cellular membrane. While the mechanism by which this occurs has not been fully elucidated, one possibility is that the lipid component may facilitate binding of the compound to the cell membrane as either a single molecule, or an aggregate (micellar) form, with subsequent internalization. However, understanding of the precise mechanism is not required for the subject compounds to be utilized.

The lipid component may be any lipid or lipid derivative that provides enhanced cellular uptake compared to the unmodified polynucleotide. Lipids of interest include, but are not limited to, hydrocarbons, fats (e.g., glycerides, fatty acids and fatty acid derivatives, such as fatty amides) and sterols. Where the lipid component is a hydrocarbon, the L component may be a substituted or unsubstituted cyclic hydrocarbon or an aliphatic straight chain or branched hydrocarbon, which may be saturated or unsaturated. Examples include straight chain unbranched hydrocarbons that are fully saturated or polyunsaturated. The length of the hydrocarbon chain may vary from C2-C30, but optimal telomerase inhibition may be obtained with carbon chains that are C8-C22. Examples of saturated hydrocarbons (alkanes) of interest are listed below:

Systematic Name/Carbon Chain
    Tetradecane $C_{14}H_{30}$
    Pentadecane $C_{15}H_{32}$
    Hexadecane $C_{16}H_{34}$
    Heptadecane $C_{17}H_{36}$
    Octadecane $C_{18}H_{38}$
    Nonadecane $C_{19}H_{40}$
    Eicosane $C_{20}H_{42}$ Mono- and poly-unsaturated forms (alkenes and polyenes, such as alkadienes and alkatrienes) of hydrocarbons may also be selected, with compounds having one to three double bonds being of interest, although compound having more double bonds may be employed. Alkynes (containing one or more triple bonds) and alkenynes (triple bond(s) and double bond(s)) may also be utilized.

Substituted forms of hydrocarbons may be employed in the subject compounds, with substituent groups that are inert in vivo and in vitro being of interest. In some cases, the substituent is fluorine. Exemplary generic structures of polyfluorinated hydrocarbons include: $CF_3(CF_2)_n$—$(CH_2)_m$— where m is at least 1, in some cases at least 2, and n is 1 to 30, such as fluorotridecane: $CF_3(CF_2)_9(CH_2)_3$; and $CH_3(CH_2)_a(CF_2)_c(CH_2)_c$— where a, b and c are independently 1-30.

Other suitable lipid components of interest include, but are not limited to, simple fatty acids and fatty acid derivatives, glycerides and more complex lipids such as sterols, for example cholesterol. Fatty acids and their derivatives of interest may be fully saturated or mono- or poly-unsaturated. The length of the carbon chain may vary from C2-C30, but optimal telomerase inhibition may be obtained with carbon chains that are C8-C22. Examples of saturated fatty acids of interest are listed below:

Systematic Name/Trivial Name/Carbon Chain
Tetradecanoic myristic 14:0
Hexadecanoic palmitic 16:0
Octadecanoic stearic 18:0
Eicosanoic arachidic 20:0

Mono- and poly-unsaturated forms of fatty acids may also be employed, with compounds having one to three double bonds being of interest, although compounds having more double bonds may also be employed. Examples of common mono- and poly-unsaturated fatty acids of interest that may be employed include:

Systematic Name/Trivial Name/Carbon Chain
Cis-9-hexadecanoic palmitoleic 16:1 (n-7)
Cis-6-octadecanoic petroselinic 18:1 (n-12)
Cis-9-octadecanoic oleic 18:1 (n-9)
9,12-octadecadienoic linoleic 18:2 (n-6)
6,9,12-octadecatrienoic gamma-linoleic 18:3 (n-6)
9,12,15-octadecatrienoic alpha-linoleic 18:3 (n-3)
5,8,11,14-eicosatetraenoic arachidonic 20:4 (n-6)

Fatty acids with one or more triple bonds in the carbon chain, as well as branched fatty acids may also be employed in the subject compounds. Substituted forms of fatty acids may be employed in the subject compounds. As with the hydrocarbon groups, substituent groups that are inert in vivo and in vitro are of interest, such as fluorine. Exemplary generic structures of polyfluorinated derivatives of fatty acids suitable for use in the invention are: $CF_3(CF_2)_n$—$(CH_2)_mCO$— where m is at least 1, preferably at least 2, and n is 1 to 30, and $CH_3(CH_2)_a(CF_2)_b(CH_2)_cCO$— where a, b and c are independently 1-30.

In some cases, between one and five L components (n is 1, 2, 3, 4 or 5) are covalently linked to the O component, via an optionally linker. In some cases, one or two L components are utilized (n=1 or 2). Where more than one L component is linked to the O component, each L component is independently selected.

It will be appreciated that compounds of the invention described as having a specified hydrocarbon as the L moiety and compounds described as having a specified fatty acid (with the same number of carbon atoms as the specified hydrocarbon) are closely related and differ in structure only in the nature of the bond that joins the L moiety to the polynucleotide, which in turn is a result of the synthesis procedure used to produce the compound. For example, and as described in more detail below, when compounds are synthesized having the L moiety conjugated to the 3'-amino terminus of a polynucleotide (having phosphoramidate or thiophosphoramidate internucleoside linkages), the use of the aldehyde form of a fatty acid (a fatty aldehyde) as the starting material results in the formation of an amine linkage between the lipid chain and the polynucleotide, such that the lipid group appears as a hydrocarbon. In contrast, use of the carboxylic acid, acid anhydride or acid chloride forms of the same fatty acid results in the formation of an amide linkage, such that the lipid group appears as a fatty acid derivative, specifically in this instance a fatty amide (as noted in the definitions section above, for the sake of simplicity, the term "fatty acid" when describing the conjugated L group is used broadly herein to include fatty acid derivatives, including fatty amides). This is illustrated in the following schematics which depict the 3'-amino terminus of a phosphoramidate polynucleotide joined to a C14 lipid component. In schematic A, L is tetradecanoic acid (myristic acid), in which the connection between L and O groups is an amide. In schematic B, L is tetradecane, and the connection between the L and O groups is an amine.

Schematic A

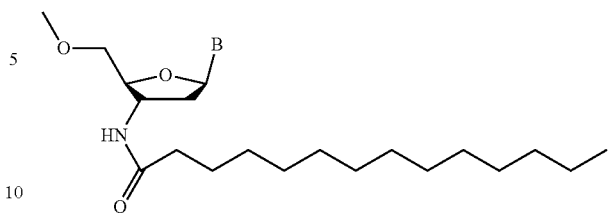

Schematic B

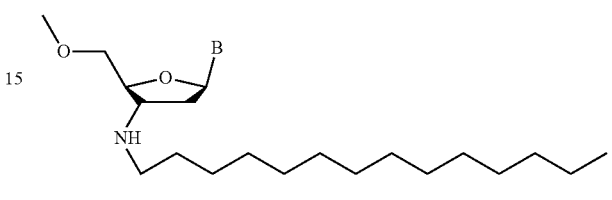

The linkage between the O and L components may be a direct linkage, or may be via an optional linker moiety, e.g., x or optional linker T of Formula (I). The linker group may serve to facilitate the chemical synthesis of the compounds. Whether or not a linker group is used to mediate the conjugation of the O and L components, there are multiple sites on the polynucleotide component O to which the L component(s) may be conveniently conjugated. Suitable linkage points include the 5' and 3' termini, one or more sugar rings, the internucleoside backbone and the nucleobases of the polynucleotide. In some cases, the L moiety is attached to the 3' or 5' terminus of the polynucleotide.

If the L component is to be attached to the 3' terminus, the attachment may be directly to the 3' substituent, which in the case of the preferred phosphoramidate and thiophosphoramidate polynucleotides is the 3'-amino group, and in other instances, such as conventional phosphodiester polynucleotides, is a 3-hydroxy group. Alternatively, the L moiety may be linked via a 3'-linked phosphate group, in which a hexadecane hydrocarbon is linked to the 3' phosphate of a thiophosphoramidate polynucleotide through an O-alkyl linker. If the L moiety is to be linked to the 5' terminus, it may be attached through a 5'-linked phosphate group. Attachment to a base on the O moiety may through any suitable atom, for example to the N2 amino group of guanosine. Where n>1 such that a plurality of lipid moieties is to be attached to the O component, the individually selected L components may be attached at any convenient site(s). For example, one L group may be attached to each terminus, various L groups may be attached to the bases, or two or more L groups may be attached at one terminus.

The optional linker component x may be used to join the O and L components of the compounds. It is understood that the optional linker (e.g., x, or T of Formula (I)) may be attached to the polynucleotide (e.g., O) through a terminal phosphate group, e.g., a 3'-linked or a 5'-linked phosphate group. If a linker is to be employed, it is incorporated into the synthesis procedures as described herein. Examples of suitable linker groups include amino glycerol and O-alkyl glycerol-type linkers which respectively can be depicted by the generic structures:

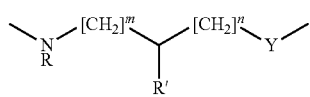

wherein R' is H, OH, NH$_2$ or SH; Y is O, S or NR; R is H, an alkyl or a substituted alkyl; and n and m are each independently integers between 1-18.
Examples of suitable linkers of interest are the aminoglycerol linker in which R' is OH, Y is O, and m and n are each 1:

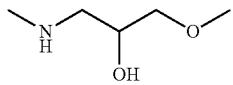

the bis-aminoglycerol linker, in which R' is OH, Y is NH, and m and n are each 1:

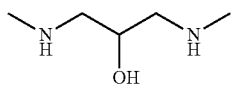

and the O-alkyl glycerol linker in which R is H:

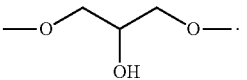

Exemplary lipid-modified polynucleotides that may be prepared according to the subject methods include those compounds described in FIG. 1 (e.g., FIGS. 1A-1DD) of U.S. Application US20120329858 to Gryaznov et al. "Modified oligonucleotides for telomerase inhibition", the disclosure of which is herein incorporated by reference in its entirety.

In certain embodiments, the composition includes a compound described by the structure:

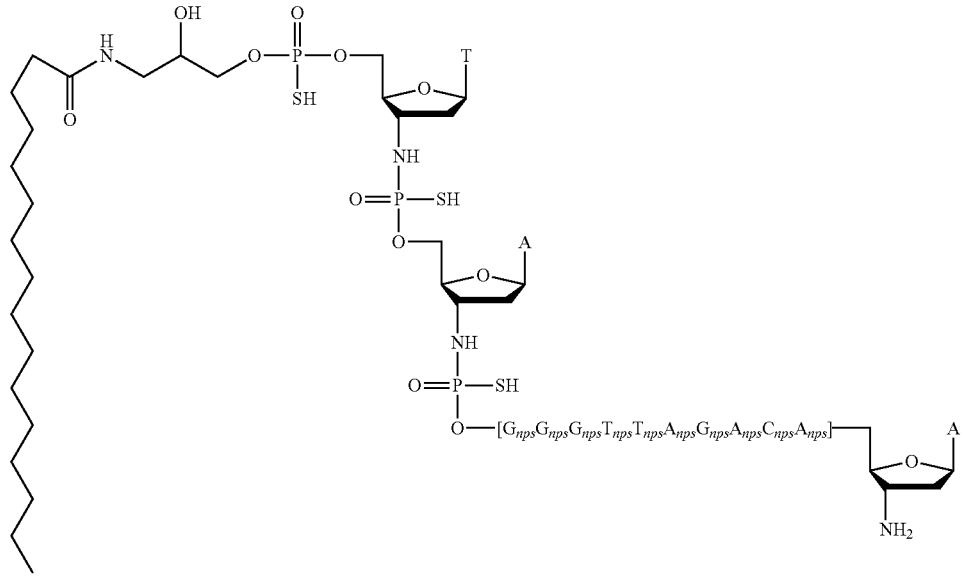

or a salt thereof, where "nps" represents a thiophosphoramidate linkage (e.g., —NH—P(=O)(SH)—O— or a tautomer thereof, or a salt thereof), connecting the 3'-carbon of one nucleoside to the 5'-carbon of the adjacent nucleoside. It is understood that the compound described in the formula above may exist in a salt form. Such forms in so far as they may exist, are intended to be included within the scope of the present disclosure. In certain embodiments, the composition includes a pharmaceutically acceptable salt of the compound. In certain instances, the composition includes a sodium salt of the compound. In certain embodiments, the composition includes a divalent cation salt of the compound, such as a magnesium salt of the compound. In certain embodiments, the composition includes a trivalent cation salt of the compound, such as an aluminium salt of the compound.

In certain embodiments, the composition includes a compound described by the following structure:

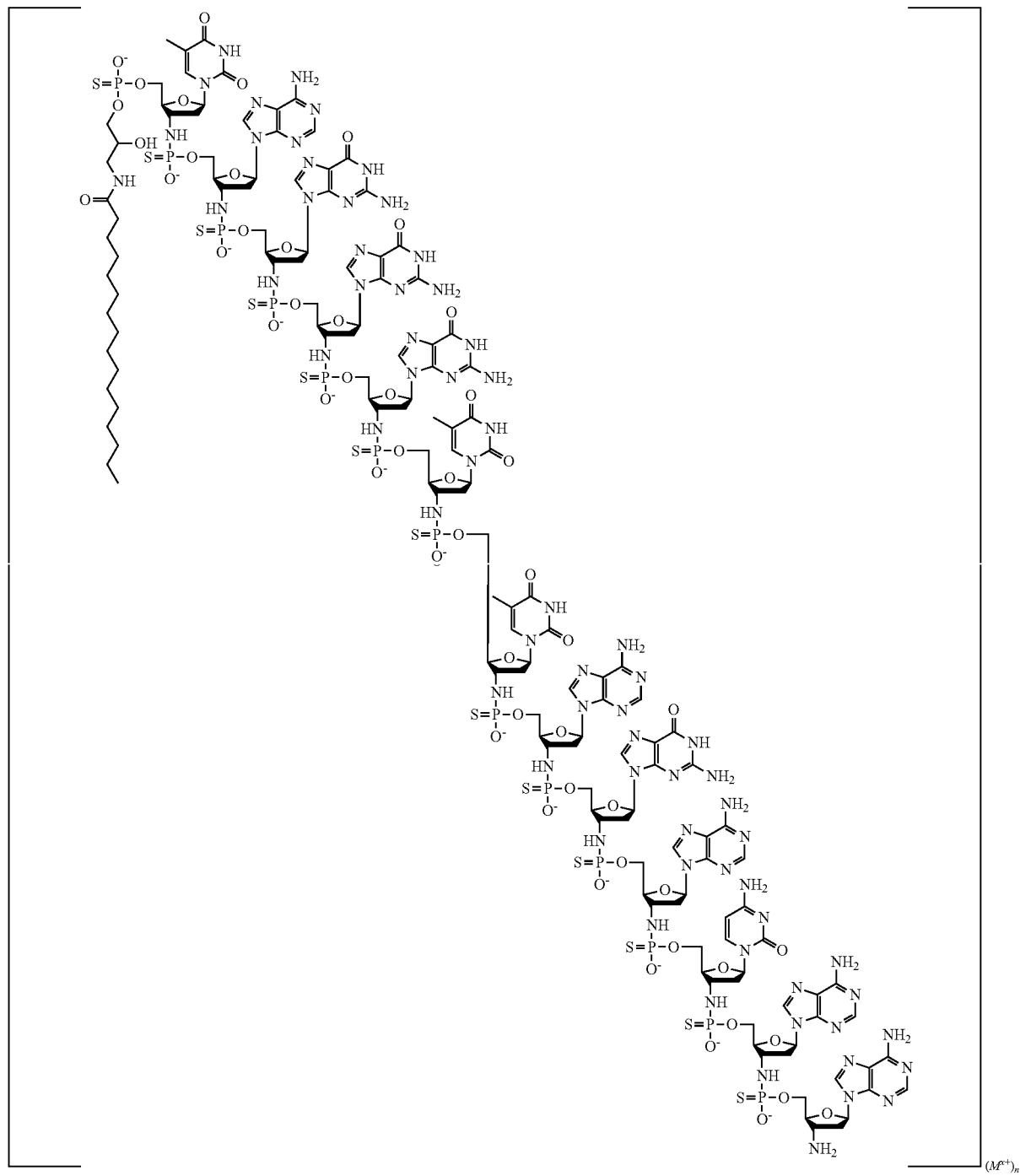

where each $M^{x+}$ is independently hydrogen or any convenient counterion of a salt, each x is independently 1, 2 or 3 and n is an integer from 5 to 13. In some instances, n is 5, 6, 7, 8, 9, 10, 11, 12 or 13. In certain instances, each x is independently 1, 2 or 3 and n is an integer from 5 to 12. In certain instances, n is 13. In certain instances, each x is 1. In certain instances, each x is independently 1 or 2. In certain instances, each x is independently 1 or 3. In certain instances, each $M^{x+}$ is independently a cationic counterion. In certain instances, each $M^{x+}$ is independently a cationic counterion, each x is independently 1, 2 or 3 and n is an integer from 5 to 12. In certain instances, each $M^{x+}$ is independently hydrogen or any convenient cationic counterion, each x is independently 1, 2 or 3 and n is an integer from 5 to 12. In certain instances, $M^{x+}$ is hydrogen. In some embodiments, $(M^{x+})_n$ is $(Mg^{2+})(M^+)_{11}$. In some embodiments, $(M^{x+})_n$ is $(Mg^{2+})_2(M^+)_9$. In some embodiments, $(M^{x+})_n$ is $(Mg^{2+})_2(M^+)_9$. In some embodiments, $(M^{x+})_n$ is $(Mg^{2+})_3(M^+)_7$. In some embodiments, $(M^{x+})_n$ is $(Mg^{2+})_4(M^+)_5$. In some embodiments, $(M^{x+})_n$ is $(Mg^{2+})_5(M^+)_3$. In some embodiments, $(M^{x+})_n$ is $(Mg^{2+})_6(M^+)$. In some embodiments, $(M^{x+})_n$ is $(Mg^{2+})(M^+)_{12}$, where the $Mg^{2+}$ counterion may form an additional ion pair to the anionic backbone of another oligonucleotide. In some embodiments, $(M^{x+})_n$ is $(Mg^{2+})_2(M^+)_{11}$, where the $Mg^{2+}$ counterions may form two an additional ion pairs to the anionic backbone(s) of one or two other oligonucleotide(s). In certain instances, the $M^+$ counterion of the mixed magnesium salt is sodium. In certain instances, the $M^+$ counterion of the mixed magnesium salt is ammonium. In certain instances, the $M^+$ counterion of the mixed magnesium salt is triethylammonium.

In certain embodiments, the composition includes a compound described by the following structure and may include any convenient cationic counterions of a salt:

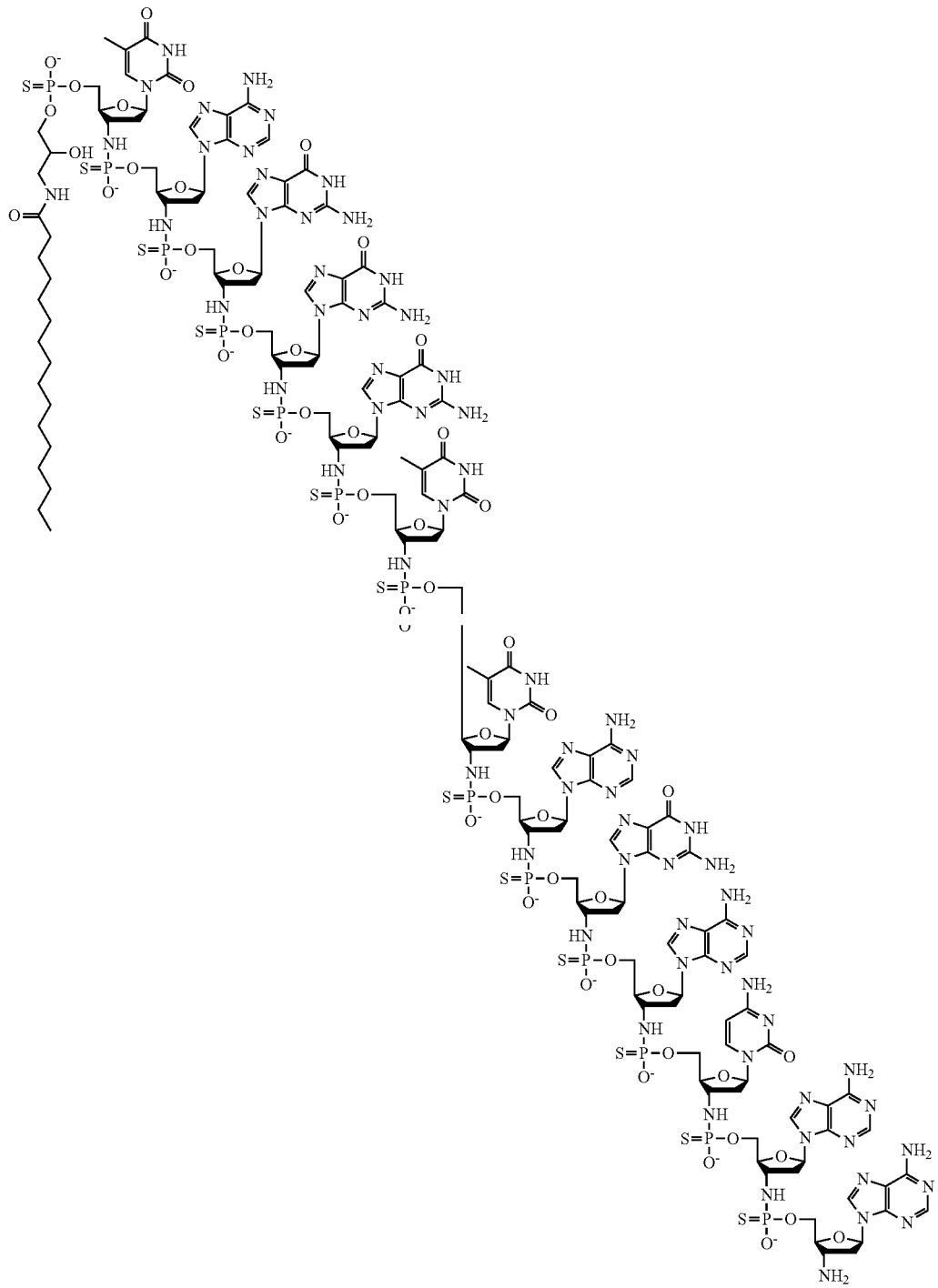

In certain embodiments, the composition includes a compound described by the structure:

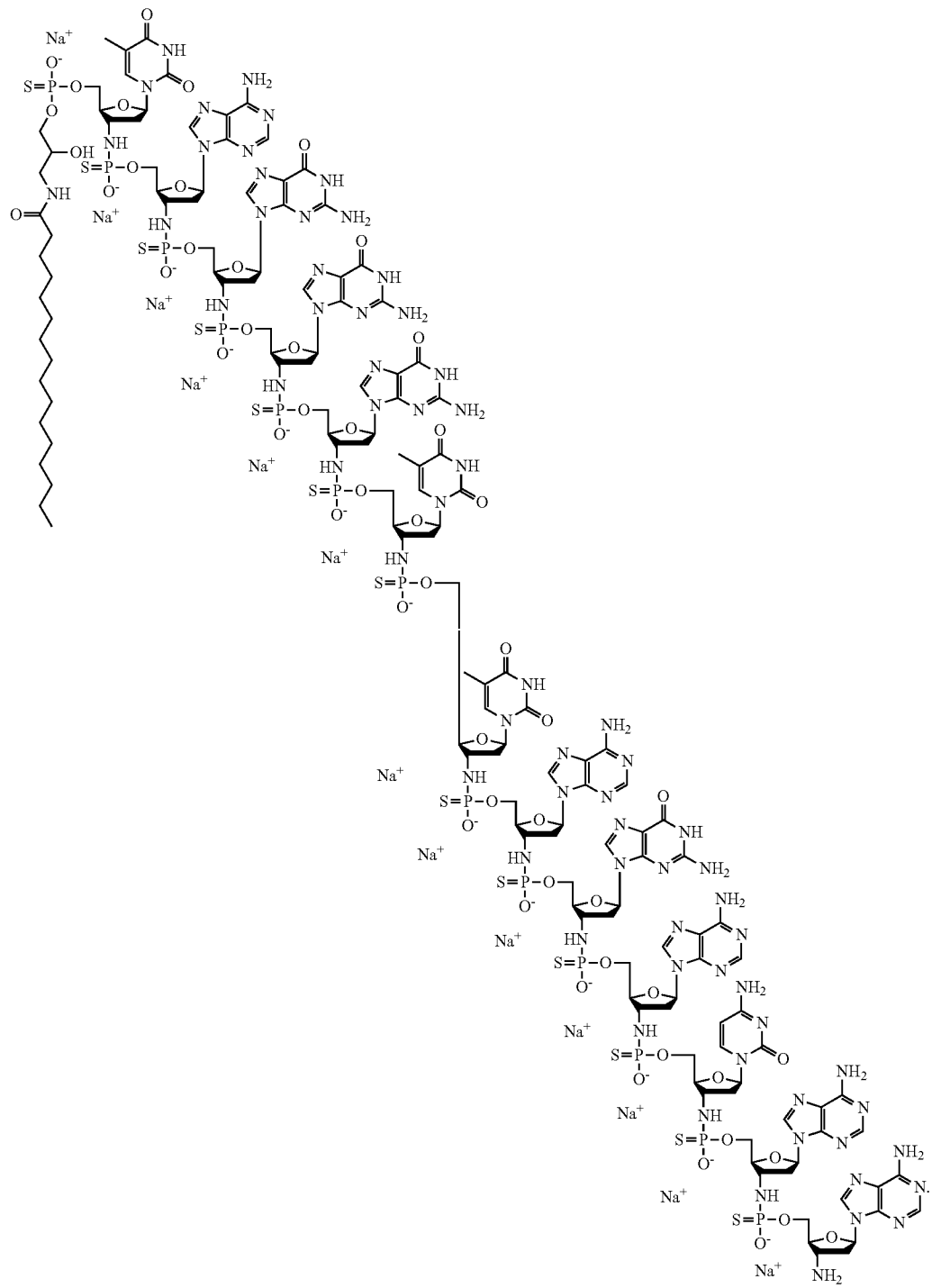

Lipid modified polynucleotides

A variety of synthetic approaches can be used to conjugate a lipid moiety L to the polynucleotide, depending on the nature of the linkage selected, including the approaches described in Mishra et al., (1995) Biochemica et Biophysica Acta, 1264:229-237, Shea et al., (1990) Nucleic Acids Res. 18:3777-3783, and Rump et al., (1998) Bioconj. Chem. 9:341-349. The synthesis of compounds in which the lipid moiety is conjugated at the 5' or 3' terminus of the polynucleotide can be achieved through use of suitable functional groups at the appropriate terminus, in some cases an amino group or a hydroxyl group, which can be reacted with carboxylic acids, acid chlorides, anhydrides and active esters. Thiol groups may also be used as functional groups (see Kupihar et al., (2001) Bioorganic and Medicinal Chemistry 9:1241-1247). Both amino- and thiol-modifiers of different chain lengths are commercially available for polynucleotide synthesis. Polynucleotides having N3'→P5'thiophosphoramidate linkages contain 3'-amino groups (rather than 3'-hydroxy found in most conventional polynucleotide chemistries), and hence these polynucleotides provide a unique opportunity for conjugating lipid groups to the 3'-end of the polynucleotide.

Various approaches can be used to attach lipid groups to the termini of polynucleotides with the N3'→P5' thiophosphoramidate chemistry (e.g., a palmitoylamido-1-O-(4,4'-dimethoxytrityl)-2-O-succinyl propanediol linker). For attachment to the 3' terminus, the conjugated compounds can be synthesized by reacting the free 3'-amino group of the fully protected solid support bound polynucleotide with the corresponding acid anhydride followed by deprotection with ammonia and purification. Alternatively, coupling of carboxylic acids of lipids to the free 3'-amino group of the support bound polynucleotide using coupling agents such as carbodiimides, HBTU (N,N,N',N'-tetramethyl-O-(1H-benzotriazol-1-yl)uronium hexafluorophosphate) or 2-chloro-1-methylpyridinium iodide can be used to conjugate the lipid groups. These two methods form an amide bond between the lipid and the polynucleotide. Lipids may also be attached to the polynucleotide chain using a phosphoramidite derivative of the lipid coupled to the polynucleotides during chain elongation. This approach yields a phosphoramidate (e.g., thiophosphoramidate) linkage connecting the lipid and the polynucleotide (exemplified by propyl-palmitoyl and 2-hydroxy-propyl-palmitoyl compounds). Still another approach involves reaction of the free 3'-amino group of the fully protected support bound polynucleotide with a suitable lipid aldehyde, followed by reduction with sodium cyanoborohydride, which produces an amine linkage.

For attachment to the 5' terminus, the polynucleotide can be synthesized using a modified, lipid-containing solid support, followed by synthesis of the polynucleotide in the 5' to 3' direction as described in Pongracz & Gryaznov (1999). An example of the modified support is provided below. In the instance where n=14, the fatty acid is palmitic acid: reaction of 3-amino-1, 2-propanediol with palmitoyl chloride, followed by dimethoxytritylation and succinylation provided the intermediate used for coupling to the solid support. In some instances, R may be long chain alkyl amine controlled pore glass. In certain instances, R is a polymeric solid support.

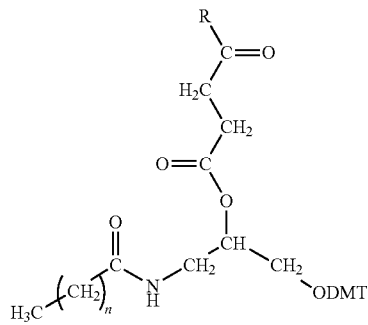

Utility

The methods and compositions of the invention, e.g., as described above, find use in a variety of applications. Applications of interest include, but are not limited to: therapeutic applications, diagnostic applications, research applications, and screening applications, as reviewed in greater detail below.

The subject compounds find use in a variety of therapeutic applications. In some embodiments, the methods of producing a polynucleotide are applied to prepare polynucleotides that provide for a therapeutic benefit. The types of diseases which are treatable using the compositions of the present invention are limitless. For example, the compositions may be used for treatment of a number of genetic diseases. In some embodiments, the subject methods and compositions have antisense applications. In some embodiments, the subject methods and compositions have antigene applications. In certain embodiments, the subject methods and compositions have telomerase inhibition applications, such as those described in U.S. Pat. No. 6,835,826, and U.S. Publication 20120329858, the disclosures of which are herein incorporated by reference in their entirety.

The present disclosure provides compounds that can specifically and potently inhibit telomerase activity, and which may therefore be used to inhibit the proliferation of telomerase-positive cells, such as tumor cells. A very wide variety of cancer cells have been shown to be telomerase-positive, including cells from cancer of the skin, connective tissue, adipose, breast, lung, stomach, pancreas, ovary, cervix, uterus, kidney, bladder, colon, prostate, central nervous system (CNS), retina and hematologic tumors (such as myeloma, leukemia and lymphoma). Cancers of interest include, but are not limited to, myelofibrosis, thrombocythemia, myelodysplastic syndrome and myelogenous leukemia.

The subject compounds can be used to treat hematologic malignancies and myeloproliferative disorders, including but not limited to, essential thrombocythemia (ET), polycythemia vera (PV) chronic myelogenous leukemia (CML), myelofibrosis (MF), chronic neutrophilic leukemia, chronic eosinophilic leukemia, and acute myelogenous leukemia (AML). The subject compounds can be used to treat myelodysplastic syndromes, which include such disease as refractory anemia, refractory anemia with excess blasts, refractory cytopenia with multilineage dysplasia, refractory cytopenia with unilineage dysplasia, and chronic myelomonocytic leukemia (CMML). The subject compounds can be used to treat hematological diseases, such as those described in PCT patent application No. PCT/US13/070437 filed Nov. 15, 2013, the disclosure of which is incorporated herein by reference in its entirety.

Accordingly, the compounds provided herein are broadly useful in treating a wide range of malignancies. In some instances, the subject compounds can be effective in providing treatments that discriminate between malignant and normal cells to a high degree, avoiding many of the deleterious side-effects present with most current chemotherapeutic regimens which rely on agents that kill dividing cells indiscriminately. Moreover, in some cases, the subject lipid modified compounds are more potent than equivalent unconjugated oligonucleotides, which means that they can be administered at lower doses, providing enhanced safety and significant reductions in cost of treatment. Telomerase inhibitors may be employed in conjunction with other cancer treatment approaches, including surgical removal of primary tumors, chemotherapeutic agents and radiation treatment. Hence, the invention relates to compounds and compositions provided herein for use as a medicament. The invention also relates to compounds and compositions provided herein for use in treating or preventing any one of the malignancies mentioned hereinbefore.

The subject compounds and methods find use in a variety of diagnostic applications, including but not limited to, the development of clinical diagnostics, e.g., in vitro diagnostics or in vivo tumor imaging agents. Such applications are useful in diagnosing or confirming diagnosis of a disease condition, or susceptibility thereto. The methods are also useful for monitoring disease progression and/or response to treatment in patients who have been previously diagnosed with the disease.

EXAMPLES

Example 1

Summary

These examples describe experiments to prepare various divalent or trivalent forms of Imetelstat, such as Ca, Ba, Mg, Al, Fe, Cu, and Zn from the sodium salt form of Imetelstat. In these experiments, improvements in purity using methods of preparation involving the formation and isolation of salts of the bi-dentate or tri-dentate cations that can bind with one, two or three phosphate groups of Imetelstat were evaluated. The solubility and osmolality of resulting salt forms were also studied.

The preparation of Imetelstat Calcium, Imetelstat Barium, Imetelstat Magnesium, Imetelstat Aluminum, Fe (II or III) Imetelstat, and Cupric Imetelstat salts were investigated using $CaCl_2$, $MgCl_2$, $BaCl_2$, $CuCl_2$, $ZnCl_2$, $AlCl_3$, $FeCl_2$, and $FeCl_3$.

Three methods for salt exchange were studied: use of a strong cation-exchange resin (FINEX MFG 210), precipitation, and simple dissolution. When the Imetelstat Sodium solution was passed through a resin exchanged with $CaCl_2$, $BaCl_2$ or $MgCl_2$, the eluate solutions contained fine powders, indicating that sodium counterions were successfully exchanged from the Imetelstat backbone and replaced with calcium, barium or magnesium counterions. For the other five reagents ($CuCl_2$, $ZnCl_2$, $AlCl_3$, $FeCl_2$, $FeCl_3$) which were equilibrated with the cation exchange resin, the top part of resin in the column became aggregated when Imetelstat solution was passed through, also indicating that sodium counterions were successfully exchanged from the Imetelstat backbone.

Precipitation and dissolution methods were also tested using an excess of salt reagents. When a large excess of salt reagent (e.g. 900 equivalents) was treated with Imetelstat Sodium, a precipitate was formed. The precipitates were isolated by filtration. Subsequent tests indicate that seven to fifty equivalents of inorganic salt reagents were necessary to convert all of the Imetelstat to a precipitate.

Five equivalents of the three inorganic salts (Mg, Ba or Ca) were each treated with either Imetelstat TEA (triethylammonium) salt form or Imetelstat Na salt form. It was confirmed that precipitation did not occur and the solutions were desalted and freeze-dried. The analysis of freeze-dried powder by Flame AA (Atomic Absorption) showed that some of the sodium counterions of Imetelstat were exchanged.

An additional experiment was performed with $MgCl_2$ using one to nine equivalents of magnesium cation to the Imetelstat form. The sodium counterions were partially exchanged to Mg counterions with the highest exchange occurring at nine equivalents of $MgCl_2$, with the resulting compositions showing 1.2% by weight of Na and 1.1% by weight of Mg.

Example 2

Materials and Equipments

The inorganic reagents, organic solvents, and other materials used for the study are listed in Table 1. Imetelstat Sodium (CAS #1007380-31-5) of Lot # of G163/L-G-13002 provided by Geron was used for the study. Imetelstat ammonium is a crude composition derived from cleavage of Imetelstat from a solid phase synthesis support using ammonia and ethanol (e.g., as described by Gryaznov et al. in US 20120329858) and was obtained from the manufacturer's stock. Imetelstat TEA (triethylammonium form) is a composition derived from an HPLC purification column eluate where a triethylammonium acetate (TEAA) containing mobile phase is used (e.g., as described by Gryaznov et al. in US 20120329858) and was obtained from the manufacturer's stock obtained from various process development studies. The ultrafiltration was performed using a Stirred Ultrafiltration Cell (Amicon 8400, Millipore) with 1KD PES membranes. The lyophilization was conducted using a Speed Vacuum Concentrator (ScanSpeed 40, LaboGene).

Example 3

Procedure

Exchange by Ion-Exchange Resin Column

A column of strong cation exchange resin, FINEX MFG 210, was prepared having a column volume of 200 mL (4.6 cm×12 cm) and the resin was washed with 1M NaOH and water. The column was then equilibrated with a 1M solution of each salt of interest. In total, eight 1M salt solutions were prepared and used ($CaCl_2$, $MgCl_2$, $BaCl_2$, $CuCl_2$, $ZnCl_2$, $AlCl_2$, $FeCl_2$, and $FeCl_3$) in these experiments. A 50 mL solution of Imetelstat sodium at 100 mg/mL was added to the column.

In case of the $CuCl_2$, $ZnCl_2$, $AlCl_2$, $FeCl_2$, and $FeCl_3$ equilibrated columns, aggregation of Imetelstat on the resin was observed in the top part of column when Imetelstat sodium was loaded onto the column.

The three columns equilibrated with $CaCl_2$, $MgCl_2$ and $BaCl_2$, salt solutions did not result in any Imetelstat aggregation on the column and Imetelstat was recovered from the column eluate, which were observed as cloudy solutions. Fine powders were recovered from these eluates by centrifugation (4000 rpm, 20 min). After centrifugation, it was confirmed that the supernatant did not contain any Imetelstat by HPLC analysis. This indicates that the precipitation and separation of calcium, magnesium and barium salts of Imetelstat was successfully achieved.

By Precipitation

The crystallization or precipitation of divalent or trivalent forms of Imetelstat was investigated using a large excess of inorganic salts of interest (900 equivalents, weight base). 1M salt solutions $CaCl_2$, $MgCl_2$, $BaCl_2$, $CuCl_2$, $ZnCl_2$, $AlCl_2$, $FeCl_2$, and $FeCl_3$ were prepared. Three types of Imetelstat solution: crude Imetelstat solution (ammonium salt), purified Imetelstat (triethylammonium (TEA) salt form), and Imetelstat sodium (Na salt form), were mixed with each salt solution.

All mixed solutions showed precipitates of Imetelstat, which were isolated easily by filtration with an Advantec 2 filter paper. This result indicates that the precipitation and separation of multivalent salts of Imetelstat was successfully achieved.

The solubilities of the precipitates isolated under the conditions of large excess of salt regent were initially investigated using the following solvents: water, acetonitrile, MeOH, EtOH, IPA (isopropyl alcohol), 0.1M NaOH, 0.1M HCl, 1M NaCl, and NMP.

For salts precipitated in a large excess of salt reagent, calcium, barium, and magnesium salts of Imetelstat were soluble in a 0.1M NaOH and 1M NaCl solution. (see Table 2). Solubility studies of Imetelstat precipitate obtained from a large excess of magnesium salt reagent were conducted in 1M NaCl solutions at different concentrations (2 mg/mL to 6 mg/mL) and under different pH conditions (pH 8, 9, 10, 11, 12) and analyzed by HPLC (see chromatograms of FIG. 1). The Imetelstat precipitate was observed to be soluble at 6 mg/mL and pH 11 to pH 12. The compound also showed stability up to pH 12 without any precipitates (FIG. 1).

By Dissolution 30 to 50 Equivalents Salt Reagent

The number of equivalents of salt reagents of interest that could achieve a complete precipitation of Imetelstat was investigated by adding the salt reagent of interest step by step. The complete formation of precipitate was observed in the range of 7 to 50 equivalents of added salt reagent for the eight salts listed in Table 3. As more equivalents of salt reagents were added, a trend towards gel formation with precipitation was observed for all salts.

Three types of Imetelstat solution were used: crude Imetelstat ammonium (crude form), Imetelstat triethylammonium (purified TEA salt form), and Imetelstat sodium (Na salt form), were mixed with each salt solution. The Imetelstat ammonium salt was used as either a $NH_4OH$ solution or a solution in water. The Imetelstat ammonium and Imetelstat TEA solutions required approximately 50 equivalents or 30 equivalents of Mg salt reagent, respectively, to achieve complete precipitation.

The solubility of precipitates formed from the Imetelstat TEA solution and the Imetelstat ammonium solution were investigated under various pH conditions from pH 8 to pH 12. After leaving the mixed solutions for 6 hrs at RT, the solubility of the Imetelstat-Mg precipitates was analyzed by UV absorbance at 260 nm. Both precipitates obtained from the Imetelstat ammonium and the Imetelstat TEA showed a similar trend in that more Imetelstat salt dissolved in 1M NaCl solution at high pH (see Table 3).

This result suggests that when the number of equivalents of salt reagent of interest relative to Imetelstat is controlled, complete precipitation of Imetelstat salt may be achieved by any convenient method to produce a precipitate that may be successfully redissolved.

5 Equivalents Salt Reagent

Figure 2:
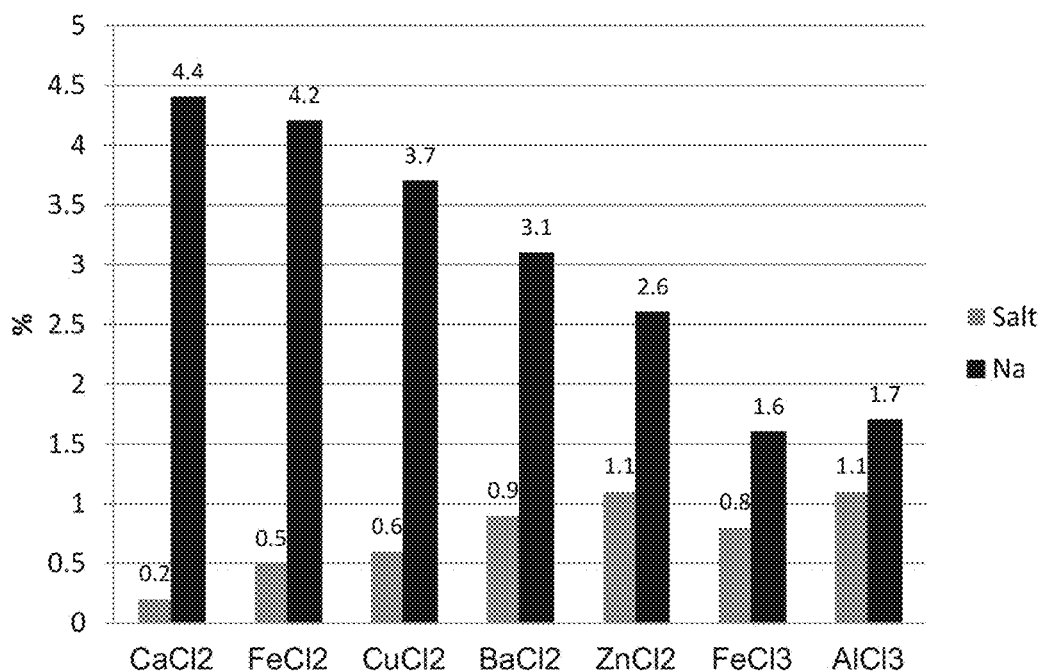
FIG. 2 depicts the results of an elemental analysis of Imetelstat Sodium treated with a variety of salts.
Figure 3:
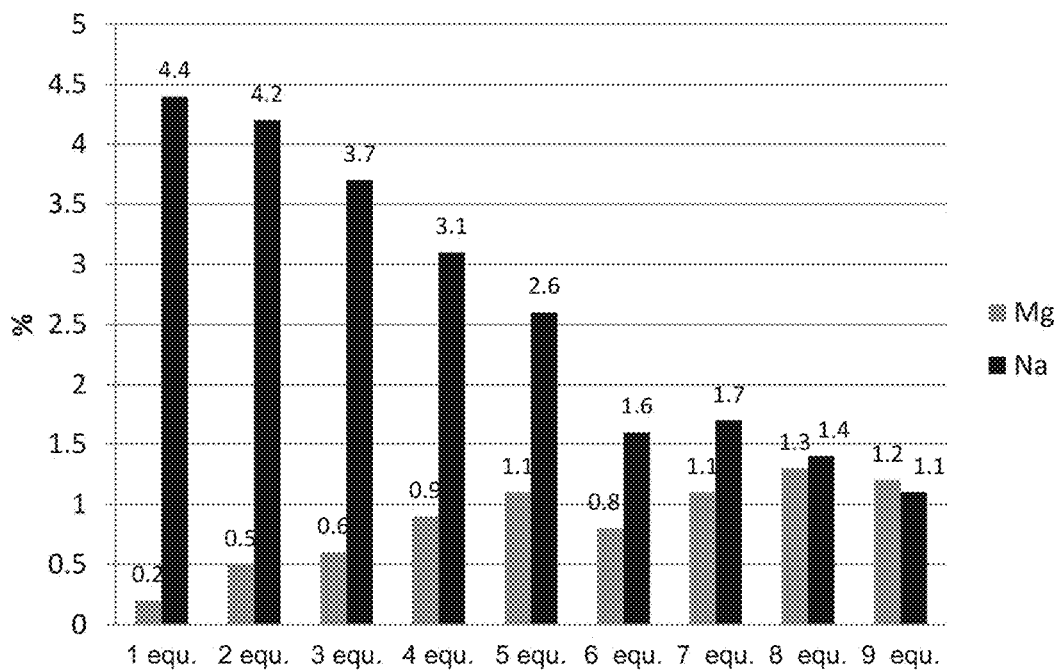
FIG. 3 depicts the results of an elemental analysis of Imetelstat Sodium treated with increasing equivalents of magnesium chloride salt.

Imetelstat Sodium solution (100 mg in 1 mL of water) was mixed with 5 equivalents of eight salt reagents and each solution was desalted by ultrafiltration using a Stirred Ultrafiltration Cell and 1KD membrane. The ultrafiltered solution was then lyophilized. The resulting powder was analyzed for the content of Na and each metal counterion of interest by Flame AA (atomic absorption spectroscopy. As show in FIGS. 2 and 3, the highest metal counterion content was 1.1% by weight for Zn, Al, and Mg, with Na contents of 2.6%, 1.7%, and 2.6%, respectively.

6 to 9 Equivalents Salt Reagent

Addition of 6 to 9 equivalents of magnesium salt reagent to Imetelstat Sodium solution was made and the subsequent ultrafiltration and lyophilzation provided the solid product which was completely soluble in water. The analysis of sodium and magnesium content was performed (see results in FIG. 3). Addition of nine equivalents of $MgCl_2$ to Imetelstat Sodium solution, produce a composition where the Na and Mg counterion content is 1.1% and 1.2% by weight, respectively.

1 to 10 Equivalents Salt Reagent

Figure 4:
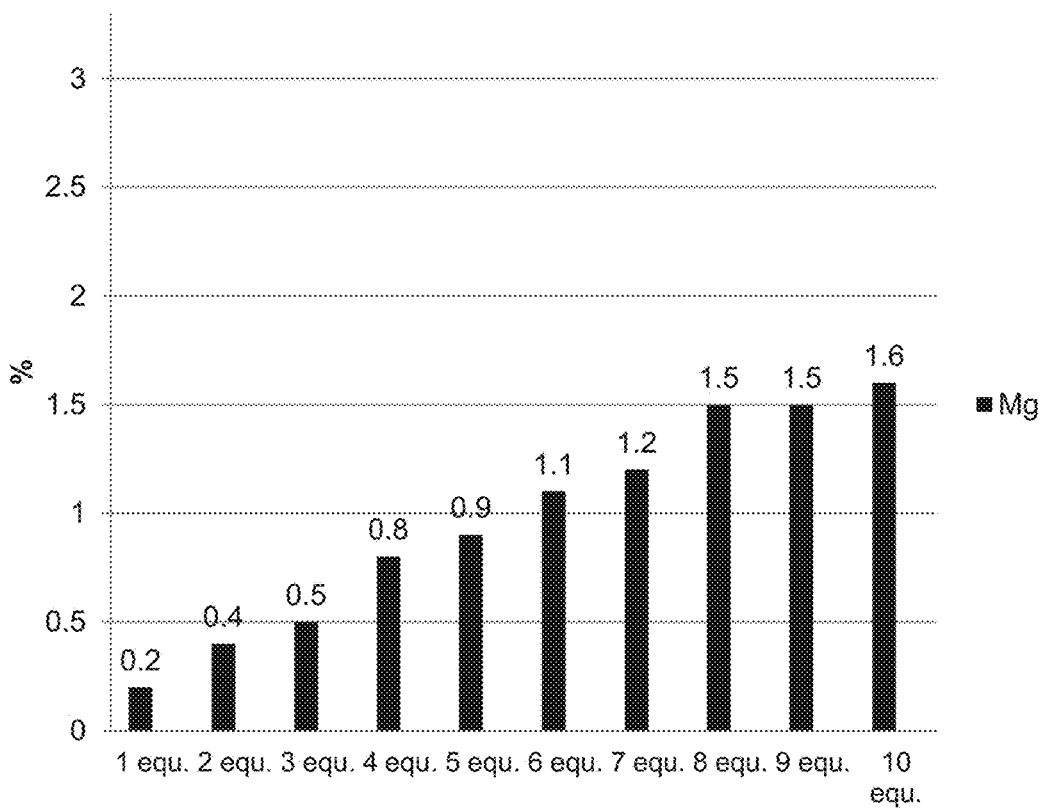
FIG. 4 depicts the results of an elemental analysis of Imetelstat TEA treated with increasing equivalents of magnesium chloride salt.

To investigate the exchange of Mg with TEA counterions in Imetelstat TEA salt as compared to Imetelstat sodium salt, another set of experiments was designed and performed. One to ten equivalents of $MgCl_2$ in aqueous solutions were mixed with Imetelstat TEA salt solution (purity >90% by HPLC). An analysis of the Mg counterion content was performed after ultrafiltration and lyophilization. The results are shown in FIG. 4. The addition of up to 10 equivalents of $MgCl_2$ reagent produced a composition having 1.6% of Mg by weight.

Example 4

Conclusion

The preparation of divalent and trivalent salt forms of Imetelstat was achieved including calcium, magnesium, zinc, aluminium, barium, iron(II), iron (III) and copper salts. When a controlled excess of selected inorganic salt reagents was used (see Table 2 and 3) to precipitate the polynucleotide, precipitates were formed which could be subsequently redissolved, and which show improved purity with respect to fast eluting impurities using HPLC analysis.

The use of a magnesium salt reagent produced a soluble solid precipitate of Imetelstat after the exchange step. Precipitates were produced which achieved a 1.2% by weight of magnesium counterion relative to 1.1% by weight of sodium counterion.

The precipitation of Imetelstat using divalent or trivalent salts provides for the removal of non-target synthetic products and reagents which remain in solution. The removal of such impurities present in crude Imetelstat solutions provides several advantages for subsequent chromatography purification steps of Imetelstat, such as reduced column loading, improved resolution, reduced number of chromatography purification steps and improved lifetime of chromatography columns, decreased purification costs and faster purifications.

TABLE 1

Inorganic Salts, Organic Solvents, and Other Materials

| Material | Molecular Formula (Molecular Weight) | Grade or Purity |
|---|---|---|
| Calcium Chloride dihydrate | $CaCl_2 \cdot 2H_2O$ (MW 147.01) | ≥99% |
| Magnesium chloride monohydrate | $MgCl_2 \cdot H_2O$ (MW 203.30) | ≥99% |
| Barium chloride dihydrate | $BaCl_2 \cdot 2H_2O$ (MW 244.26) | ≥99% |
| Copper(II) chloride dihydrate | $CuCl_2 \cdot 2H_2O$ (MW 170.48) | ≥99% |
| Zinc chloride | $ZnCl_2$ (MW 136.30) | ≥98% |
| Aluminum chloride hexahydrate | $AlCl_3 \cdot 6H_2O$ (MW 241.43) | ≥95% |
| Iron (II) chloride tetrahydrate | $FeCl_2 \cdot 4H_2O$ (MW 198.81) | ≥98% |
| Iron (III) chloride hexahydrate | $FeCl_3 \cdot 6H_2O$ (MW 270.30) | ≥98% |
| Sodium chloride | NaCl (MW 58.4) | USP grade |

TABLE 2

(○: Yes, X: No, "—" means not performed)

| Method | Imetelstat Tested | Test Performed | $CaCl_2$ | $MgCl_2$ | $BaCl_2$ | $CuCl_2$ | $ZnCl_2$ | $AlCl_3$ | $FeCl_2$ | $FeCl_3$ |
|---|---|---|---|---|---|---|---|---|---|---|
| Ion Exchange Resin | Sodium (Na form, 100 mg/mL) | Column Pass through | ○ | ○ | ○ | X | X | X | X | X |
| | | Precipitation in solution after | ○ | ○ | ○ | — | — | — | — | — |

TABLE 2-continued (○: Yes, X: No, "—" means not performed)

| Method | Imetelstat Tested | Test Performed | CaCl$_2$ | MgCl$_2$ | BaCl$_2$ | CuCl$_2$ | ZnCl$_2$ | AlCl$_3$ | FeCl$_2$ | FeCl$_3$ |
|---|---|---|---|---|---|---|---|---|---|---|
| | | column Filtration of precipitates | X | X | X | — | — | — | — | — |
| | | Solubility* of Precipitate | X | X | X | — | — | — | — | — |
| Precipitation (900 equivalent) | Sodium (Na form, 100 mg/mL) | Precipitates (Filterable) | ○ | ○ | ○ | ○ | ○ | ○ | ○ | ○ |
| | | Solubility** of Precipitate | X | X | X | X | X | X | X | X |
| | | Solubility of Precipitate in 1M NaOH | ○ | ○ | ○ | X | X | X | X | X |
| | TEA (35 mg/mL) | Precipitates (Filterable) | ○ | ○ | ○ | ○ | ○ | ○ | ○ | ○ |
| | | Solubility** of Precipitate | X | X | X | X | X | X | X | X |
| | | Solubility of Precipitate in 1M NaOH | ○ | ○ | X | X | X | X | X | X |
| | Crude (in NH$_4$OH) | Precipitates (Filterable) | ○ | ○ | ○ | ○ | ○ | ○ | ○ | ○ |
| | | Solubility** of Precipitate | X | X | X | — | — | — | — | — |

*Tested in Acetonitrile, MeOH, EtOH, IPA, Water, NMP, 1M HCl, 1M NaCl, 1M NaOH
**Tested in Acetonitrile, MeOH, EtOH, IPA, Water, NMP, 1M HCl, 1M NaCl

TABLE 3

| Dissolution | Sodium | Inorganic Salt | 9 | 15 | 12 | 7 | 50 | 50 | 10 | 11 |
|---|---|---|---|---|---|---|---|---|---|---|
| | TEA | Equivalents to | 15 | 30 | 30 | 10 | 50 | 10 | 50 | 10 |
| | Crude (in NH$_4$OH) | get complete precipitation | — | >50 | — | — | — | — | — | — |
| | Crude (in water) | | — | 30 | — | — | — | — | — | — |

| Solubility In 1M NaCl (1 mL) | TEA | Imetelstat-Mg ppt 6 mg (After 64 hours) | pH 8 28 OD | pH 9 31 OD | pH 10 70 OD | pH 11 290 OD | pH 12 434 OD |
|---|---|---|---|---|---|---|---|
| | Crude (in water) | Imetelstat-Mg ppt 6 mg (After 6 hours) | pH 8 10 OD | pH 9 7 OD | pH 10 17 OD | pH 11 111 OD | pH 12 377 OD |

Notwithstanding the appended claims, the disclosure set forth herein is also defined by the following clauses:

1. A method of preparing a polynucleotide, the method comprising:
   contacting a first polynucleotide composition comprising:
   a polynucleotide having a sequence of 7 or more nucleoside subunits and at least two of the nucleoside subunits are joined by a N3'→P5' thiophosphoramidate inter-subunit linkage; and
   non-target synthetic products and reagents;
   with a multivalent cation salt to precipitate a first polynucleotide salt comprising at least one multivalent cation counterion; and
   separating the first polynucleotide salt from the contacted first polynucleotide composition to produce a second polynucleotide composition comprising the first polynucleotide salt.

2. The method of clause 1, further comprising: contacting the first polynucleotide salt with a reverse phase chromatography support; and eluting from the chromatography support a third polynucleotide composition comprising a second polynucleotide salt.

3. The method of any one of clauses 1-2, wherein the polynucleotide comprises a sequence comprising 13 or more nucleoside subunits complementary to the RNA component of human telomerase.

4. The method of any one of clauses 1-3, wherein the polynucleotide comprises between 10 and 50 contiguous nucleoside subunits complementary to the RNA component of human telomerase.

5. The method of any one of clauses 3-4, wherein the nucleoside subunits complementary to the RNA component of human telomerase are all joined by N3'→P5' thiophosphoramidate inter-subunit linkages.

6. The method of any one of clauses 1-5 wherein the polynucleotide comprises a sequence selected from the group consisting of: GTTAGGGTTAG (SEQ ID NO:4), TAGGGTTAGACAA (SEQ ID NO:3) and CAGTTAGGGTTAG (SEQ ID NO:5).

7. The method of any one of clauses 1-6, wherein the polynucleotide is conjugated to a lipid moiety via an optional linker.

8. The method of any one of clauses 2-7, wherein the second polynucleotide salt has the structure:

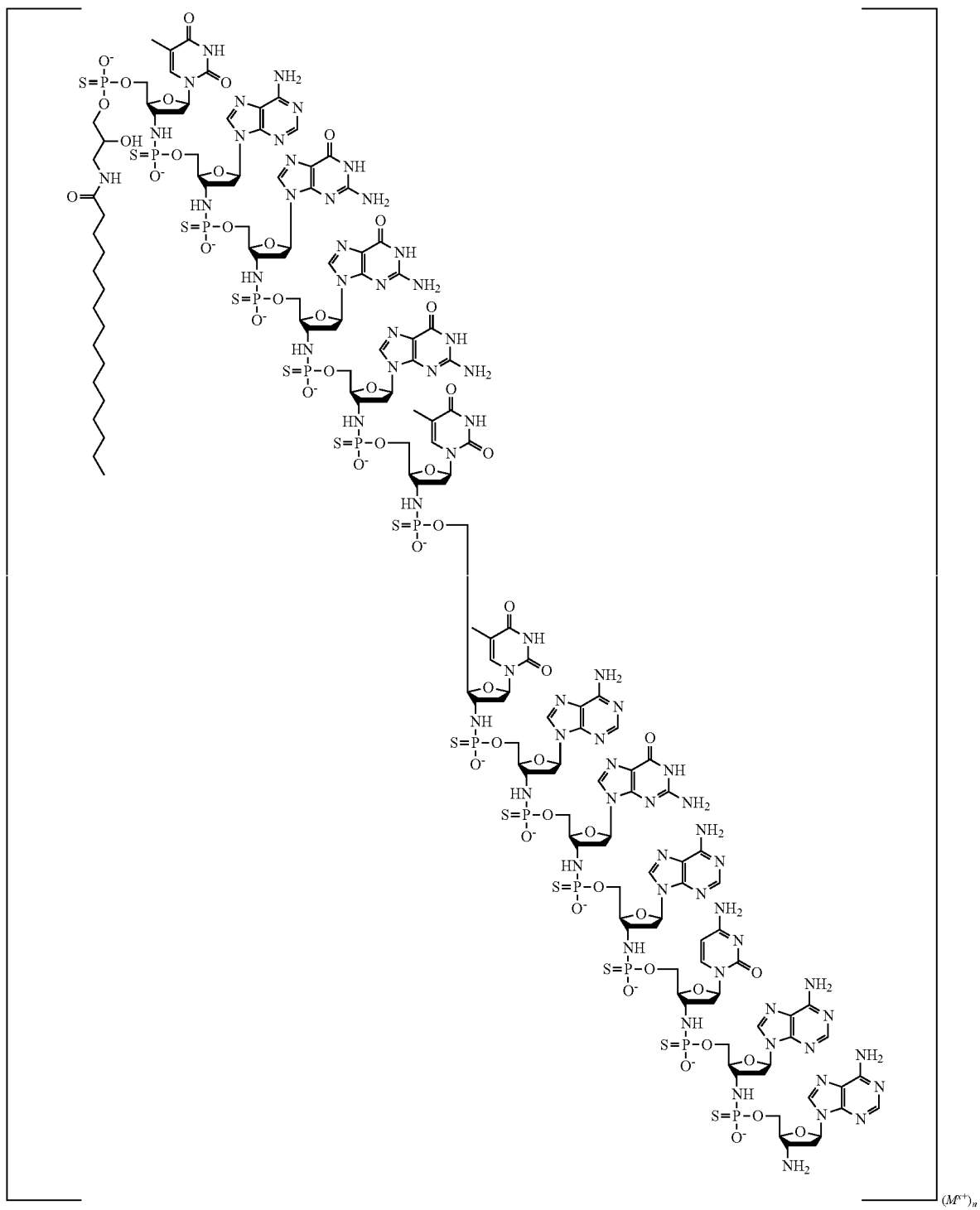

wherein each $M^{x+}$ is independently hydrogen or a cationic counterion, each x is independently 1, 2 or 3 and n is an integer from 5 to 13.

9. The method of any one of clauses 2-8, wherein the second polynucleotide salt is a pharmaceutically acceptable salt of the polynucleotide.

10. The method of any one of clauses 2-9, wherein the second polynucleotide salt is a monovalent cation salt of the polynucleotide.

11. The method of any one of clauses 2-10, wherein the second polynucleotide salt is a sodium salt of the polynucleotide.

12. The method of any one of clauses 1-5, further comprising cleaving the polynucleotide from a support to produce the first polynucleotide composition.

13. The method of any one of clauses 1-12, wherein the first composition comprises a monovalent cation salt of the polynucleotide.

14. The method of any one of clauses 1-13, wherein the contacting step comprises eluting the first polynucleotide composition from a cation exchange support.

15. The method of any one of clauses 1-14, wherein the separating step comprises centrifuging the contacted first polynucleotide composition to spin down the polynucleotide salt precipitate.

16. The method of any one of clauses 1-15, wherein the separating step comprises filtering the polynucleotide salt from the contacted first polynucleotide.

17. The method of clause 2, wherein the second polynucleotide composition is loaded directly onto the reverse phase chromatography support.

18. The method of any one of clauses 1-17, further comprising dissolving the second polynucleotide composition in a solvent.

19. The method of any one of clauses 1-18, wherein the at least one multivalent cation counterion is divalent.

20. The method of clause 19, wherein the at least one multivalent cation counterion is selected from the group consisting of magnesium, zinc and calcium.

21. The method of any one of clauses 1-18, wherein the at least one multivalent cation counterion is trivalent.

22. The method of clause 21, wherein the at least one multivalent cation counterion is aluminium.

23. The method of any one of clauses 1-22, wherein the polynucleotide salt further comprises a monovalent cation counterion.

24. A composition comprising: a salt of a polynucleotide comprising at least one multivalent cation counterion; wherein the polynucleotide has a sequence of 7 or more nucleoside subunits complementary to the RNA component of human telomerase and at least two of the nucleoside subunits are joined by a N3'→P5' thiophosphoramidate inter-subunit linkage.

25. The composition of clause 24, wherein the at least one multivalent cation counterion is divalent.

26. The composition of clause 25, wherein the at least one multivalent cation counterion is selected from the group consisting of magnesium, zinc and calcium.

27. The composition of any one of clauses 24-26, wherein the at least one multivalent cation counterion is magnesium.

28. The composition of clause 24, wherein the at least one multivalent cation counterion is trivalent.

29. The composition of clause 28, wherein the at least one multivalent cation counterion is aluminium.

30. The composition of any one of clauses 24-29, wherein the polynucleotide comprises 3 mol % or more of the multivalent cation counterion relative to a polyanionic backbone of the polynucleotide.

31. The composition of any one of clauses 24-29, wherein the polynucleotide comprises 1.0% by weight or more of the multivalent cation counterion relative to the polynucleotide.

32. The composition of any one of clauses 24-31, wherein the composition is a precipitate.

33. The composition of any one of clauses 24-32, wherein the polynucleotide comprises a sequence comprising 13 or more nucleoside subunits complementary to the RNA component of human telomerase.

34. The composition of any one of clauses 24-33, wherein the polynucleotide comprises between 10 and 50 contiguous nucleoside subunits complementary to the RNA component of human telomerase.

35. The composition of any one of clauses 24-34, wherein the nucleoside subunits complementary to the RNA component of human telomerase are all joined by N3'→P5' thiophosphoramidate inter-subunit linkages.

36. The composition of any one of clauses 24-35, wherein the polynucleotide comprises a sequence selected from the group consisting of: GTTAGGGTTAG (SEQ ID NO:4), TAGGGTTAGACAA (SEQ ID NO:3) and CAGTTAGGGTTAG (SEQ ID NO:5).

37. The composition of any one of clauses 24-36, wherein the polynucleotide is conjugated to a lipid moiety via an optional linker.

38. The composition of any one of clauses 24-37, wherein the polynucleotide has the structure:

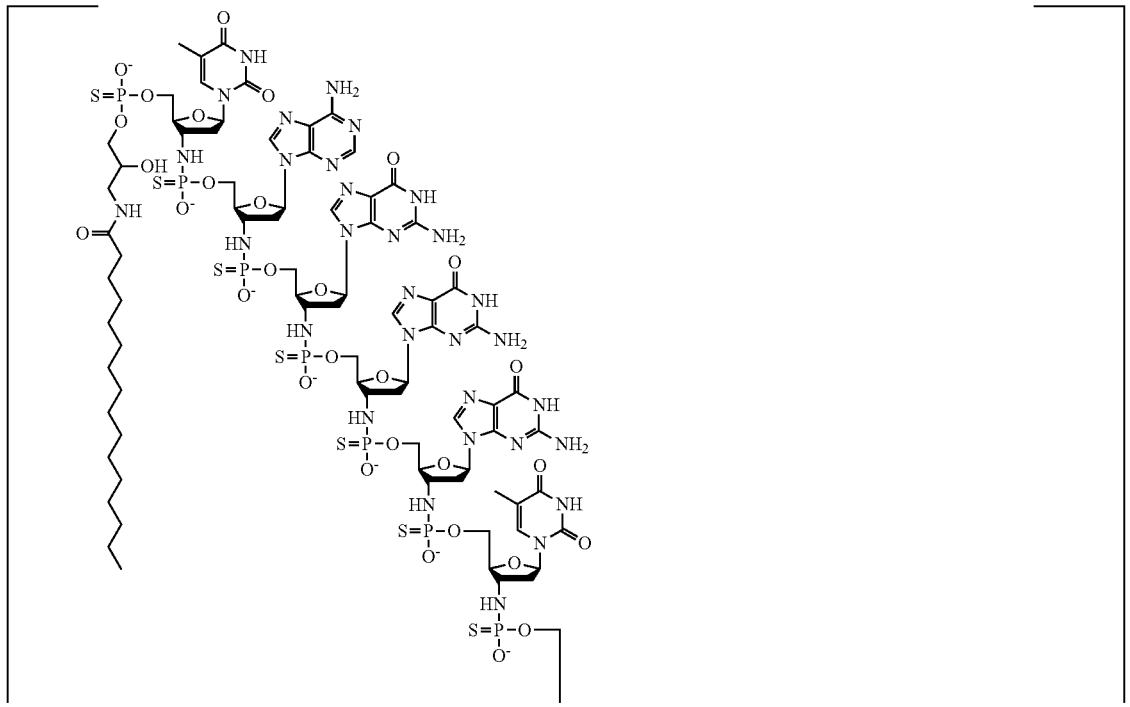

-continued

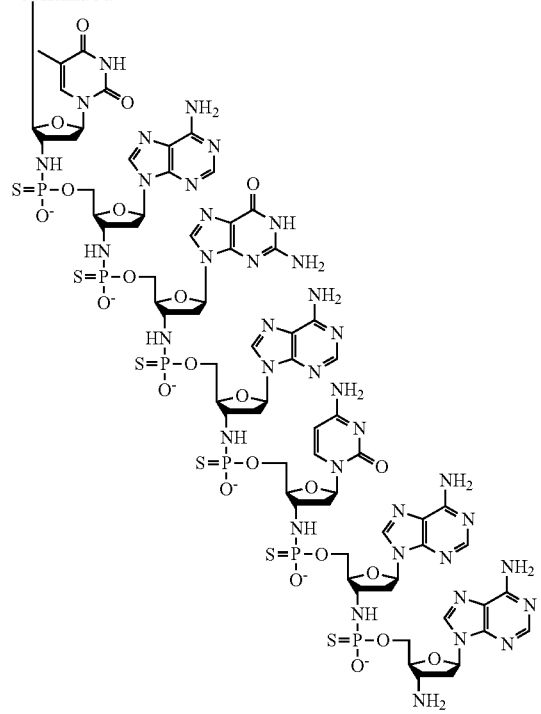

wherein each $M^{x+}$ is independently a cationic counterion, each x is 1, 2 or 3 and n is 5 to 12.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended embodiments. All possible combinations of the above-indicated embodiments are considered to be embraced within the scope of this invention.

What is claimed is:

1. A method of preparing a polynucleotide, the method comprising:
   a) contacting a first polynucleotide composition with a multivalent cation salt to precipitate a first polynucleotide salt comprising at least one multivalent cation counterion;
   b) separating the first polynucleotide salt from the contacted first polynucleotide composition to produce a second polynucleotide composition comprising the first polynucleotide salt;
   wherein the first polynucleotide composition comprises:
      (i) a polynucleotide having a sequence of 7 or more nucleoside subunits and at least two of the nucleoside subunits are joined by a N3'→P5' thiophosphoramidate inter-subunit linkage; and
      (ii) soluble non-target synthetic products and reagents;
   c) contacting the second polynucleotide composition comprising the first polynucleotide salt from step (b) with a reverse phase chromatography support; and
   d) eluting from the reverse phase chromatography support a third polynucleotide composition comprising a second soluble polynucleotide salt.

2. The method of claim 1, wherein the polynucleotide comprises a sequence comprising 13 or more nucleoside subunits complementary to the RNA component of human telomerase.

3. The method of claim 1, wherein the polynucleotide comprises between 10 and 50 contiguous nucleoside subunits complementary to the RNA component of human telomerase.

4. The method of claim 2, wherein the nucleoside subunits complementary to the RNA component of human telomerase are all joined by N3'→P5' thiophosphoramidate inter-subunit linkages.

5. The method of claim 1, wherein the polynucleotide comprises a sequence selected from the group consisting of: GTTAGGGTTAG (SEQ ID NO:4), TAGGGTTAGACAA (SEQ ID NO:3) and CAGTTAGGGTTAG (SEQ ID NO: 5).

6. The method of claim 1, wherein the polynucleotide is conjugated to a lipid moiety via an optional linker.

7. The method of claim 1, wherein the second polynucleotide salt has the structure:

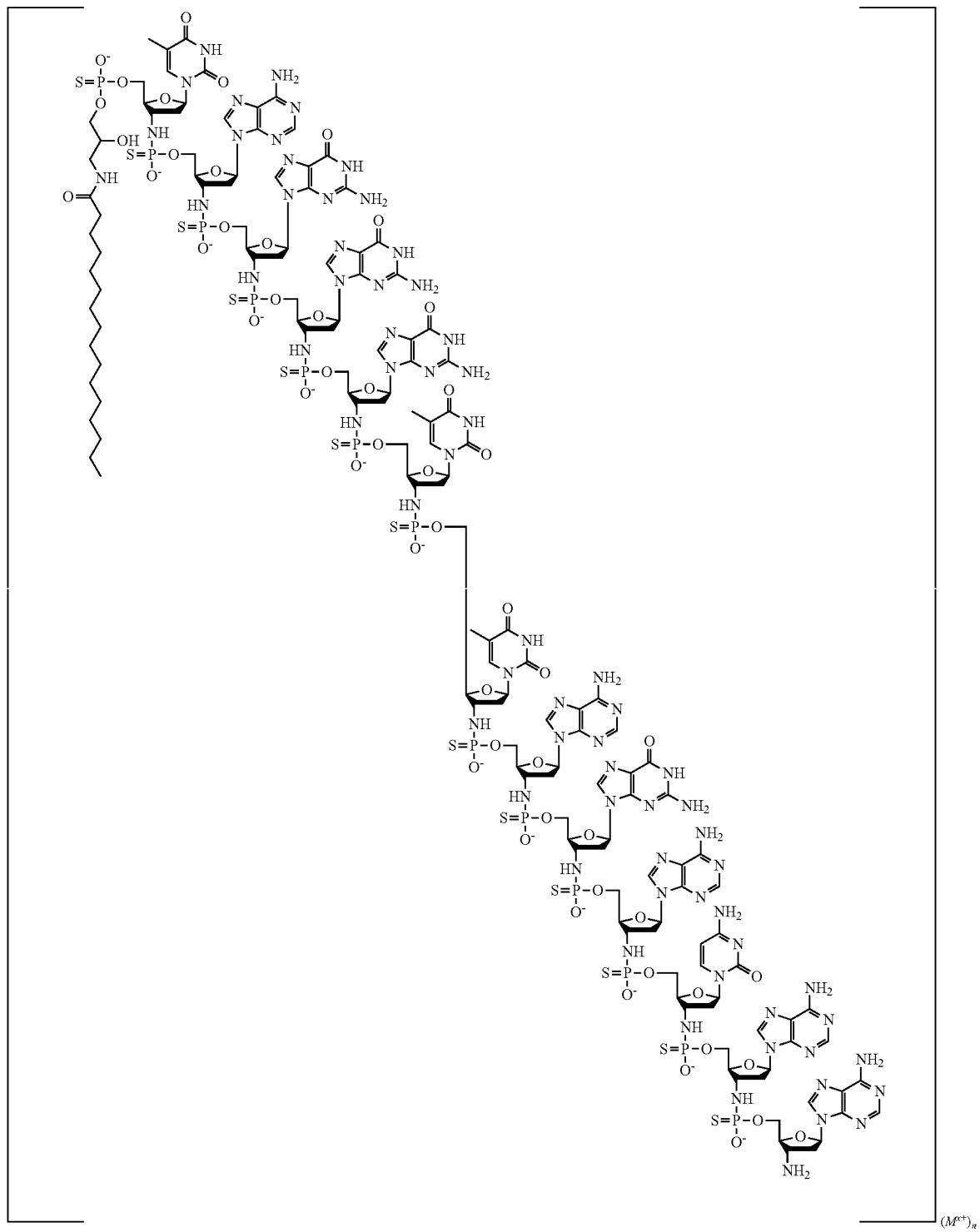

wherein each $M^{x+}$ is independently hydrogen or a cationic counterion, each x is independently 1, 2 or 3 and n is an integer from 5 to 13.

8. The method of claim 1, wherein after the eluting step d) the second polynucleotide salt is a pharmaceutically acceptable salt of the polynucleotide.

9. The method of claim 1, wherein after the eluting step d) the second polynucleotide salt is a monovalent cation salt of the polynucleotide.

10. The method of claim 9, wherein the second polynucleotide salt is a sodium salt of the polynucleotide.

11. The method of claim 1, further comprising, prior to the contacting step a), cleaving the polynucleotide from a solid phase synthesis support to produce the first polynucleotide composition as a crude synthetic preparation of the polynucleotide.

12. The method of claim 1, wherein prior to the contacting step a) the first polynucleotide composition comprises a monovalent cation salt of the polynucleotide.

13. The method of claim 1, wherein the contacting step a) comprises loading and eluting the first polynucleotide composition from a cation exchange support.

14. The method of claim 1, wherein the separating step b) comprises centrifuging the contacted first polynucleotide composition to spin down the first polynucleotide salt precipitate.

15. The method of claim 1, wherein the separating step b) comprises filtering the first polynucleotide salt from the contacted first polynucleotide composition.

16. The method of claim 1, wherein the second polynucleotide composition of step b) is loaded directly onto the reverse phase chromatography support.

17. The method of claim 1, further comprising, prior to the contacting step c), dissolving the second polynucleotide composition in a solvent.

18. The method of claim 1, wherein the at least one multivalent cation counterion is divalent.

19. The method of claim 18, wherein the at least one multivalent cation counterion is selected from the group consisting of magnesium, zinc and calcium.

20. The method of claim 1, wherein the at least one multivalent cation counterion is trivalent.

21. The method of claim 20, wherein the at least one multivalent cation counterion is aluminium.

22. The method of claim 1, wherein the first polynucleotide salt further comprises a monovalent cation counterion.

23. The method of claim 1, wherein the polynucleotide is described by Formula (I):

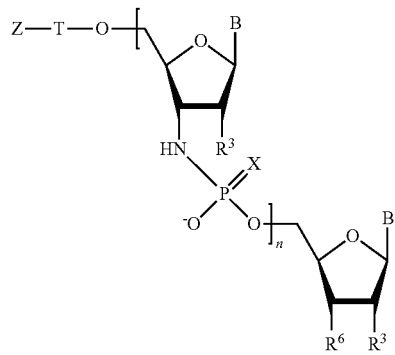

wherein:
  each B is independently a purine, a protected purine, a pyrimidine or a protected pyrimidine, or an analog thereof;
  each X is independently oxygen or sulfur;
  each $R^3$ is independently hydrogen, fluoro, hydroxyl, an alkoxy, a substituted alkoxy or a protected hydroxyl;
  $R^6$ is amino, hydroxyl, a protected amino, a protected hydroxy, —O-T-Z or —NH-T-Z;
  each T is independently an optional linker;
  each Z is independently H, a lipid, a carrier, an oligonucleotide, a polymer, a polypeptide, a detectable label, or a tag; and
  n is an integer of 7 to 100.

24. The method of claim 1, wherein the nucleoside subunits are all joined by inter-subunit linkages each independently selected from N3'→P5' thiophosphoramidate inter-subunit linkage and N3'→P5' phosphoramidate inter-subunit linkage.

* * * * *

UNITED STATES PATENT AND TRADEMARK OFFICE
CERTIFICATE OF CORRECTION

PATENT NO. : 10,745,687 B2
APPLICATION NO. : 15/134740
DATED : August 18, 2020
INVENTOR(S) : Premchandran H. Ramiya Page 1 of 1

It is certified that error appears in the above-identified patent and that said Letters Patent is hereby corrected as shown below:

In the Specification

At Column 24, Line 47:
Delete "2.8" and replace it with --2.8%--.

At Column 30, Line 36:
Delete "N3" and replace it with --N3' →P5'--.

At Column 32, Line 60:
Delete "$CH_3(CH_2)_a(CF_2)_c(CH_2)_c$" and replace it with --$CH_3(CH_2)_a(CF_2)_b(CH_2)_c$--.

In the Claims

At Column 64, Claim 2, Line 51:
Delete "13or" and replace it with --13 or--.

At Column 64, Claim 3, Line 55:
Delete "10and" and replace it with --10 and--.

At Column 65, Claim 7, Line 63:
Delete "or3" and replace it with --or 3--.

Signed and Sealed this
Twentieth Day of October, 2020

Andrei Iancu
*Director of the United States Patent and Trademark Office*

SEQUENCE LISTING

```
<160> NUMBER OF SEQ ID NOS: 23

<210> SEQ ID NO 1
<211> LENGTH: 451
<212> TYPE: RNA
<213> ORGANISM: Artificial Sequence
<220> FEATURE:
<223> OTHER INFORMATION: Synthetic oligonucleotide

<400> SEQUENCE: 1
ggguugcgga ggguggggccu gggagggggug guggccauuu uuugucuaac ccuaacugag      60
aagggcguag gcgccgugcu uuugcucccc gcgcgcuguu uuucucgcug acuuucagcg     120
ggcggaaaag ccucggccug ccgccuucca ccguucauuc uagagcaaac aaaaaauguc     180
```

```
agcugcuggc cguucgccc cucccgggga ccugcggcgg gucgccugcc cagcccccga    240
accccgccug gaggccgcgg ucggcccggg gcuucuccgg aggcacccac ugccaccgcg    300
aagaguuggg cucugucagc cgcgggucuc ucggggcga gggcgagguu caggccuuuc    360
aggccgcagg aagaggaacg gagcgagucc ccgcgcgcgg cgcgauuccc ugagcugugg    420
gacgugcacc caggacucgg cucacacaug c                                   451

<210> SEQ ID NO 2
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 2
gctctagaat gaacggtgga aggcggcagg                                     30

<210> SEQ ID NO 3
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 3
tagggttaga caa                                                       13

<210> SEQ ID NO 4
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 4
gttagggtta g                                                         11

<210> SEQ ID NO 5
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 5
cagttagggt tag                                                       13

<210> SEQ ID NO 6
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 6
gtggaaggcg gcagg                                                     15

<210> SEQ ID NO 7
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 7
```
ggaaggcggc agg                                                          13

<210> SEQ ID NO 8
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 8
gtggaaggcg gca                                                          13

<210> SEQ ID NO 9
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 9
gtggaaggcg g                                                            11

<210> SEQ ID NO 10
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 10
cggtggaagg cgg                                                          13

<210> SEQ ID NO 11
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 11
acggtggaag gcg                                                          13

<210> SEQ ID NO 12
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 12
aacggtggaa ggcggc                                                       16

<210> SEQ ID NO 13
<211> LENGTH: 18
<212> TYPE: DNA

```
<213> ORGANISM: Artificial Sequence
<220> FEATURE:
<223> OTHER INFORMATION: Synthetic oligonucleotide

<400> SEQUENCE: 13
atgaacggtg gaaggcgg                                                    18

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14 acatttttg tttgctctag                                                   20

<210> SEQ ID NO 15
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 15
tagggttaga caa                                                         13

<210> SEQ ID NO 16
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 16
gttagggtta g                                                           11

<210> SEQ ID NO 17
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 17
gttagggtta gac                                                         13

<210> SEQ ID NO 18
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 18
gttagggtta gacaa                                                       15

<210> SEQ ID NO 19
<211> LENGTH: 12
<212> TYPE: DNA
<213> ORGANISM: Artificial Sequence
<220> FEATURE:
```

```
<223> OTHER INFORMATION: Synthetic oligonucleotide

<400> SEQUENCE: 19
cccttctcag tt                                                            12

<210> SEQ ID NO 20
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 20
cgcccttctc ag                                                            12

<210> SEQ ID NO 21
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 21 gggttagac                                                                 9

<210> SEQ ID NO 22
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 22 cagttaggg                                                                 9

<210> SEQ ID NO 23
<211> LENGTH: 11
<212> TYPE: RNA
<213> ORGANISM: Artificial Sequence
<220> FEATURE:
<223> OTHER INFORMATION: Synthetic oligonucleotide

<400> SEQUENCE: 23
cuaacccuaa c                                                             11
```